United States Patent [19]
Chowrira et al.

[11] Patent Number: 6,022,962
[45] Date of Patent: *Feb. 8, 2000

[54] HAIRPIN RIBOZYMES

[75] Inventors: Bharat Chowrira, Lafayette; James A. McSwiggen, Boulder, both of Colo.

[73] Assignee: Ribozyme Pharmaceutical, Inc., Boulder, Colo.

[*] Notice: This patent is subject to a terminal disclaimer.

[21] Appl. No.: 09/098,293

[22] Filed: Jun. 16, 1998

Related U.S. Application Data

[63] Continuation of application No. 08/773,297, Dec. 23, 1996, Pat. No. 5,837,855, which is a continuation of application No. 08/321,993, Oct. 11, 1994, Pat. No. 5,631,359.

[51] Int. Cl.[7] .............................. C07H 21/02; C12N 5/06; C12N 5/08
[52] U.S. Cl. ...................... 536/24.5; 435/325; 435/355; 435/366
[58] Field of Search ................... 435/320.1, 325, 435/355; 536/24.5

[56] References Cited

U.S. PATENT DOCUMENTS

| | | | |
|---|---|---|---|
| 5,334,711 | 8/1994 | Sproat et al. | 536/24.5 |
| 5,631,359 | 5/1997 | Chowrira et al. | 536/24.5 |

FOREIGN PATENT DOCUMENTS

| | | |
|---|---|---|
| 0 360 257 | 3/1990 | European Pat. Off. . |
| 0 519 463 | 12/1992 | European Pat. Off. . |
| 91/03162 | 3/1991 | WIPO . |
| 92/07065 | 4/1992 | WIPO . |
| 93/15187 | 8/1993 | WIPO . |
| 93/23569 | 11/1993 | WIPO . |
| 94/02595 | 2/1994 | WIPO . |
| 94/13688 | 6/1994 | WIPO . |

OTHER PUBLICATIONS

Anderson et al., "Mutagenesis of the hairpin ribozyme," *Nucleic Acids Research* 22:1096–1100 (1994).
Ballantyne et al., "Nucleotide sequence of the cDNA for murine intercellular adhesion molecule–1 (ICAM–1)," *Nucleic Acids Research* 17:5853 (1989).
Barinaga, "Ribozymes: Killing the Messenger," *Science* 262:1512–1514 (1993).
Benseler et al., "Hammerhead–like Molecules Containing Non–Nucleoside Linkers Are Active RNA Catalysts," *J. Am. Chem. Soc.* 115:8483–8484 (1993).
Berzal–Herranz et al., "Essential nucleotide sequences and secondary structure elements of the hairpin ribozyme," *EMBO J.* 12:2567–2574 (1993).
Berzal–Herranz et al., "In vitro selection of active hairpin ribozymes by sequential RNA–catalyzed clevage and ligation reactions," *Genes & Development* 6:129–134 (1992).
Carter, "Adeno–Associated Virus Vectors," *Curr Opi. Biotech.* 3:533–539 (1992).
Cech, "Ribozyme Engineering," *Current Opinion in Structural Biology* 2:605–609 (1992).

Chen et al., "Multitarget–Ribozyme Directed to Cleave at up to Nine Highly Conserved HIV–1 env RNA Regions Inhibits HIV–1 Replication–Potential Effectiveness Against Most Presently Sequenced HIV–1 Isolates," *Nucleic Acids Research* 20:4581–4589 (1992).
Chowrira and Burke, "Binding and Cleavage of Nucleic Acids by the "Hairpin" Ribozyme," *Biochemistry* 30:8518–8522 (1991).
Chowrira and Burke, "Extensive Phosphorothioate Substitution Yields Highly Active and Nuclease–Resistant Hairpin Ribozymes," *Nucleic Acids Research* 20:2835–2840 (1992).
Chowrira et al., "Four Ribose 2'–Hydroxyl Groups Essential for Catalytic Function of the Hairpin Ribozyme," *J. Biol. Chem.* 268:19458–19462 (1993).
Cotten, "The in vivo application of ribozymes," *Tibtech* 8:174–178 (1990).
Edgington, "Ribozymes: Stop Making Sense," *Biotechnology* 10:256–262 (1992).
Elroy–Stein and Moss, "Cytoplasmic Expression System Based on Constitutive Synthesis of Bacteriophage T7 Polymerase in Mammalian Cells," *Proc. Natl. Acad. Sci. USA* 87:6743–6747 (1990).
Feldstein et al., "Specific association between an endoribonucleolytic sequence from a satellite RNA and a substrate analogue containing a 2'–5' phosphodiester," *Proc. Natl. Acad. Sci. USA* 87:2623–2627 (1990).
Feldstein et al., "Two sequences participating in the autolytic processing of satellite tobacco ringspot virus complementary RNA," *Gene* 82:53–61 (1989).
Gao and Huang, "Cytoplasmic Expression of a Reporter Gene by Co–Delivery of T7 RNA Polymerase and T7 Promoter Sequence with Cationic Liposomes," *Nucleic Acids Research* 21:2867–2872 (1993).
Hampel and Tritz, "RNA Catalytic Properties of the Minimum (")sTRSV Sequence," *Biochemistry* 28:4929–4933 (1989).
Hampel et al., "The Hairpin Ribozyme," *Methods: A Companion to Methods in Enzymology* 5:37–42 (1993).
Hampel et al., "'Hairpin' Catalytic RNA Model: Evidence for Helices and Sequence Requirement for Substrate RNA," *Nucleic Acids Research* 18:299–304 (1990).
Haseloff and Gerlach, "Sequences required for self–catalysed cleavage of the satellite RNA of tobacco ringspot virus," *Gene* 82:43–52 (1989).
Haseloff and Gerlach, "Simple RNA Enzymes with New and Highly Specific Endoribonuclease Activities," *Nature* 334:585–591 (1988).

(List continued on next page.)

*Primary Examiner*—Robert A. Schwartzman
*Attorney, Agent, or Firm*—Lyon & Lyon LLP

[57] ABSTRACT

Hairpin ribozyme lacking a substrate moiety, comprising atleast six bases in helix 2 and able to base-pair with a separate substrate RNA, wherein the said ribozyme comprises one or more bases 3' of helix 3 able to base-pair with the said substrate RNA to form a helix 5 and wherein the said ribozyme can cleave and/or ligate said separate RNA(s) in trans.

12 Claims, 16 Drawing Sheets

OTHER PUBLICATIONS

Hegg et al., "Kinetics and thermodynamics of intermolecular catalysis by hairpin ribozymes," *Biochemistry* 34:15813–15828 (1995).

Hisamatsu et al., "Acquirement of hairpin ribozyme activity by the long substrate–binding site," *Nucleic Acids Symposium Series No. 29* pp. 173–174 (1993).

Jeffries and Symons, "A Catalytic 13–mer Ribozyme," *Nucleic Acids Research* 17:1371–1377 (1989).

Joseph et al., "Substrate selection rules for the hairpin ribozyme determined by in vitro selection, mutation, and analysis of mismatched substrates," *Genes & Development* 7:130–138 (1993).

Kashani–Sabet et al., "Reversal of the Malignant Phenotype by an Anti–ras Ribozyme," *Antisense Research & Development* 2:3–15 (1992).

Kita et al., "Sequence and expression of rat ICAM–1," *Biochem. Biophys. Acta* 1131:108–110 (1992).

Komatsu et al., "Cross–ligation and exchange reactions catalyzed by hairpin ribozymes," *Nucleic Acids Research* 21:185–190 (1993).

Komatsu et al., "Loop–Size Variation to Probe a Bent Structure of a Hairpin Ribozyme," *J. Am. Chem. Soc.* 116:3692–3696 (1994).

L'Huillier et al., "Cytoplasmic Delivery of Ribozymes Leads to Efficient Reduction in Lactalbumin mRNA Levels in C1271 Mouse," *EMBO J.* 11:4411–4418 (1992).

Lieber et al., "Stable High–Level Gene Expression in Mammalian Cells by T7 Phage RNA Polymerase," *Methods Enzymol.* 217:47–66 (1993).

Lisziewicz et al., "Inhibition of Human Immunodeficiency Virus Type 1 Replication by Regulated Expression of a Polymeric Tat Activation Response RNA Decoy as a Strategy for Gene Therapy in AIDS," *Proc. Natl. Acad. Sci. U.S.A.* 90:8000–8004 (1993).

Ojwang et al., "Inhibition of Human Immunodefiency Virus Type 1 Expression by a Hairpin Ribozyme," *Proc. Natl. Acad. Sci. USA* 89:10802–10806 (1992).

Ortigao et al., "Antisense Effects of Oligodeoxynucleotides with Inverted Terminal Internucleotidic Linkages: A Minimal Modification Protecting Against Nucleolytic Degradation," *Antisense Research and Development* 2:129–146 (1992).

Perreault et al., "Mixed Deoxyribo– and Ribo–Oligonucleotides with Catalytic Activity," *Nature* 344:565–567 (1990).

Pieken et al., "Kinetic Characterization of Ribonuclease–Resistant 2'–Modified Hammerhead Ribozymes," *Science* 253:314–317 (1991).

Scaringe et al., "Chemical synthesis of biologically active oligoribonucleotides using cyanoethyl protected ribonucleoside phosphoramidites," *Nucl. Acids Res.* 18:5433–5441 (1990).

Simons et al., "ICAM, an adhesion ligand LFA–1, is homologous to the neutral cell adhesion molecule NCAM," *Nature* 331:624–627 (1988).

Uhlenbeck, "A Small Catalytic Oligoribonucleotide," *Nature* 328:596–600 (1987).

Usman et al., "Exploiting the chemical synthesis of RNA," *TIBS* 17:334–339 (1992).

Usman et al., "Automated Chemical Synthesis of Long Oligoribonucleotides Using 2'–O–Silylated Ribonucleoside 3'–O–Phosphoramidites on a Controlled–Pore Glass Support: Synthesis of a 43–Nucleotide Sequence Similar to the 3'–Half Molecule of an *Escherichia coli* Formylmethoionine tRNA," *J. Am. Chem. Soc.* 109:7845–7854 (1987).

van Tol et al., "Evidence for Spontaneous Circle Formation in the Replication of the Satellite RNA of Tobacco Ringspot Virus," *Virology* 180:23–30 (1991).

von Ashen and Schroeder, "RNA as a Catalyst: Natural and Designed Ribozymes," *BioEssays* 15:299–307 (1993).

Woolf et al., "Specificity of Antisense Oligonucleotides in vivo," *Proc. Natl. Acad. Sci. USA* 89:7305–7309 (1992).

Yu et al., "A Hairpin Ribozyme Inhibits Expression of Diverse Strains of Human Immunodeficiency Virus Type 1," *Proc. Natl. Acad. Sci. USA* 90:6340–6344 (1993).

Zabner et al., "Adenovirus–Mediated Gene Transfer Transiently Corrects the Chloride Transport Defect in Nasal Epithelia of Patients with Cystic Fibrosis," *Cell* 75:207–216 (1993).

Zhou et al., "Synthesis of Functional mRNA in Mammalian Cells by Bacteriophage T3 RNA Polymerase," *Mol. Cell. Biol.* 10:4529–4537 (1990).

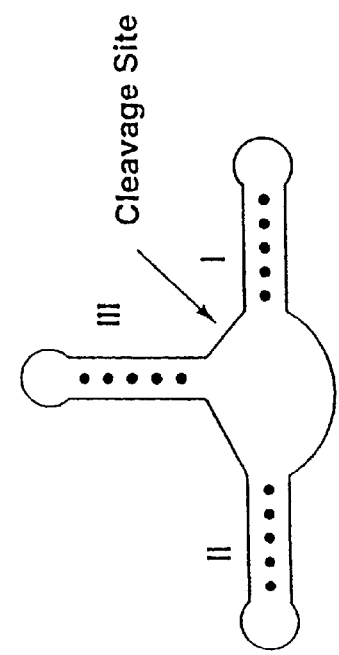
Fig. 2A
Fig. 2B
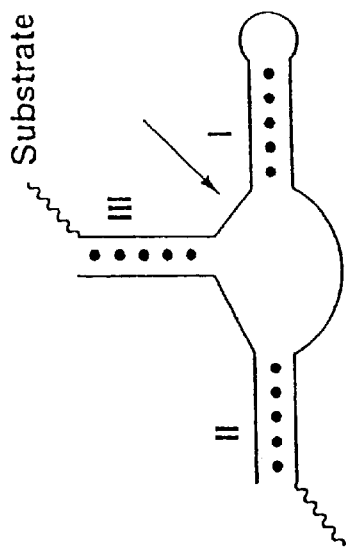
Fig. 2C
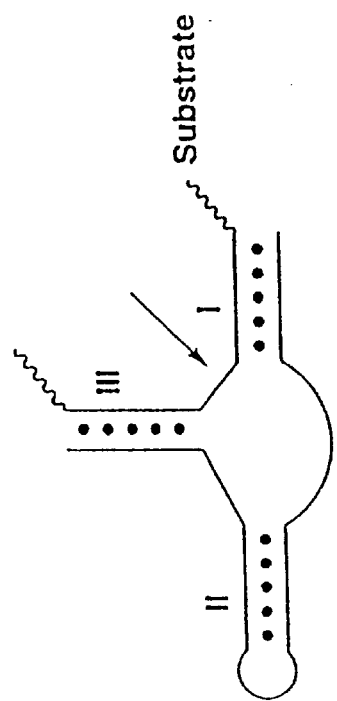
Fig. 2D

HAIRPIN RIBOZYME

HAIRPIN RIBOZYME 4 bp H2
12 bp H1

HP-A1

6 bp H2
12 bp H1

HP-A2

4 bp H2
6 bp H1

HP-B1

6 bp H2
6 bp H1

HP-B2

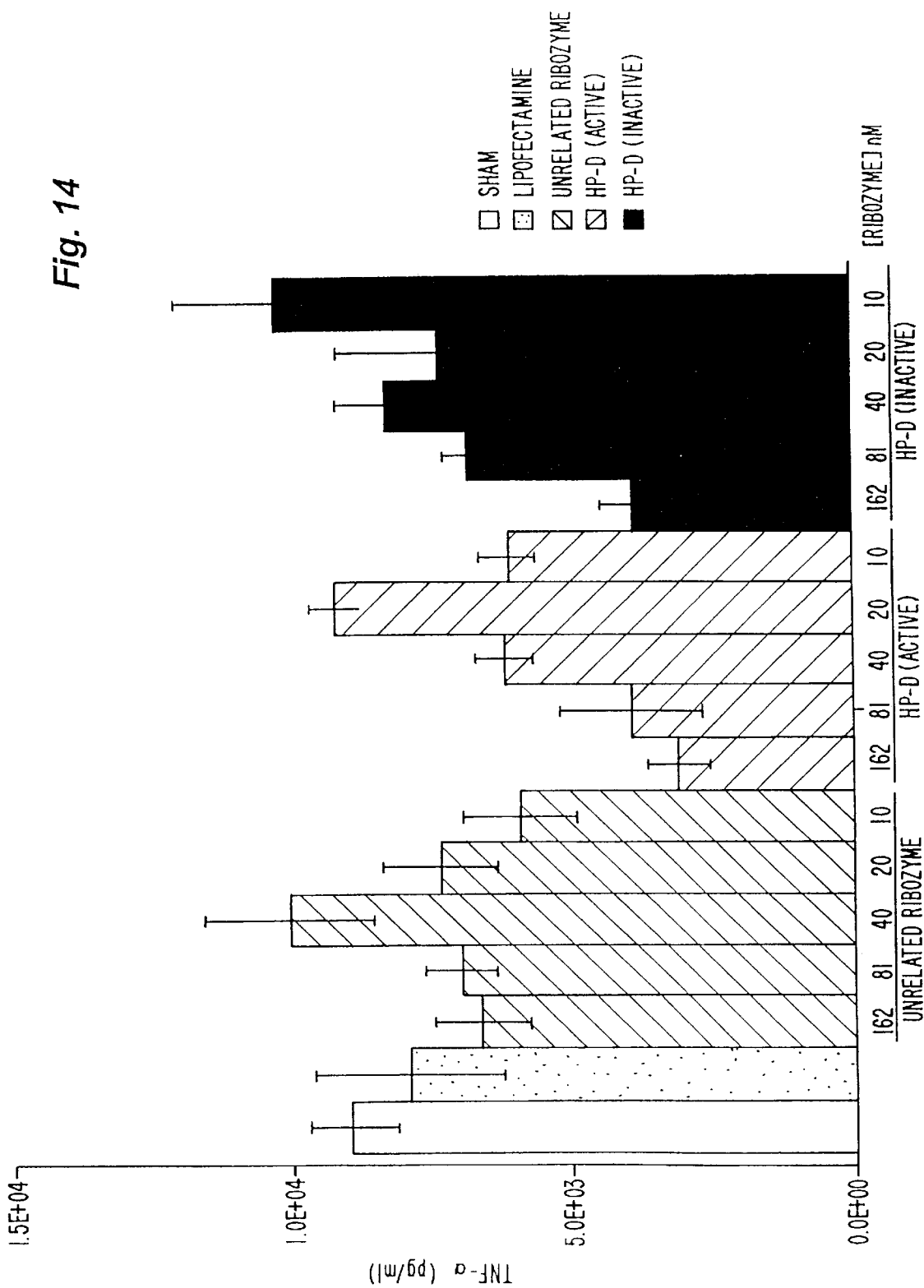

HP-E (ACTIVE)

HP-E (INACTIVE)

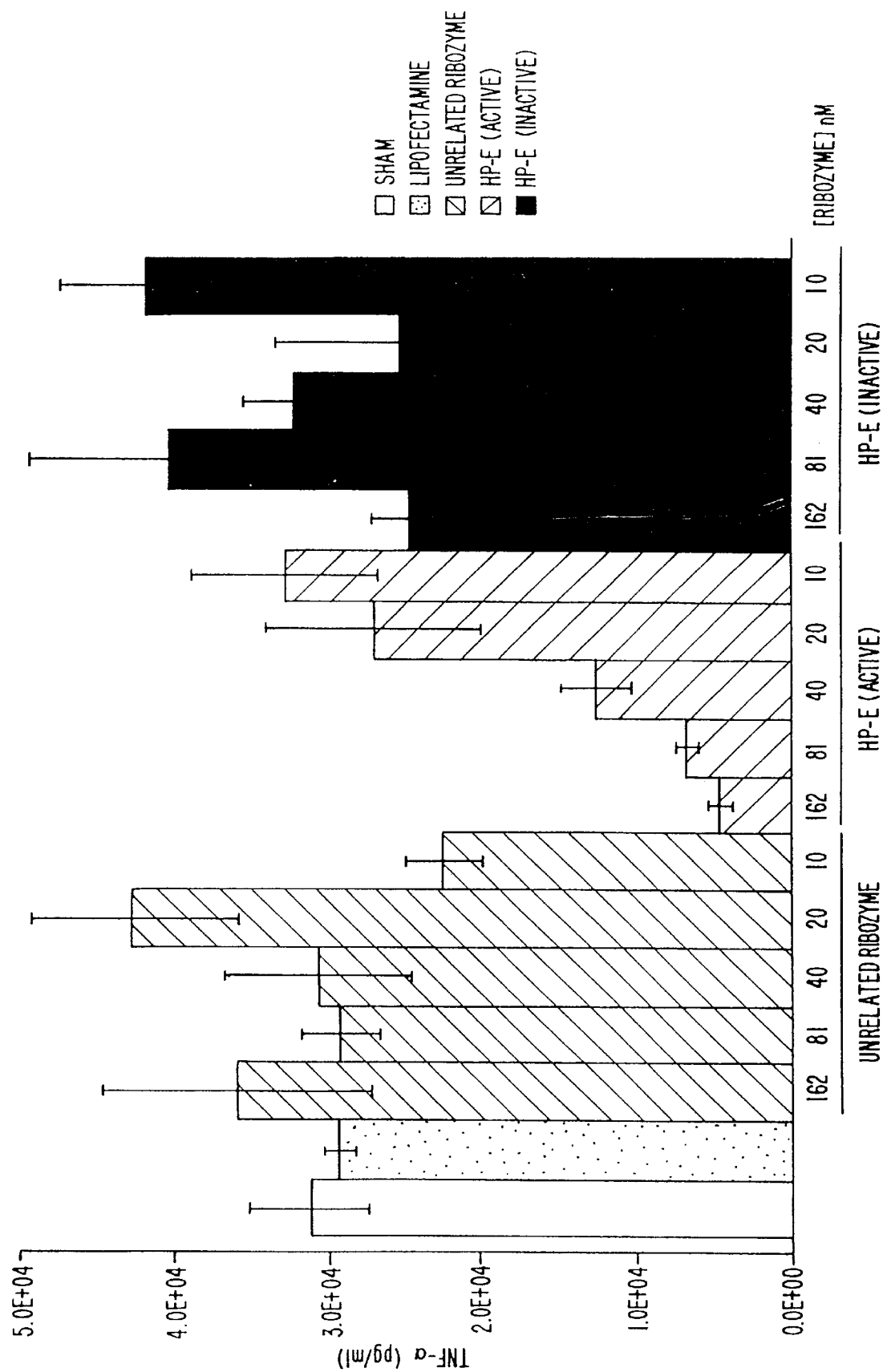

HAIRPIN RIBOZYME

HAIRPIN RIBOZYME

HAIRPIN RIBOZYME

HAIRPIN RIBOZYME

6,022,962

HAIRPIN RIBOZYMES

This Application is a continuation of U.S. Ser. No. 08/773,297 filed Dec. 23, 1996, now U.S. Pat. No. 5,837, 855, which is a continuation of U.S. Ser. No. 08/321,993, filed Oct. 11, 1994 and now U.S. Pat. No. 5,631,359. The entirety of each of these applications, including the drawings, are hereby incorporated by reference herein.

BACKGROUND OF THE INVENTION

The following is a brief description of publications concerning ribozymes, and in particular, hairpin ribozymes. none are admitted to be the prior art to the pending claims, and all are incorporated by reference herein.

Six basic varieties of naturally-occurring enzymatic RNAs are known presently. Each can catalyze the hydrolysis of RNA phosphodiester bonds in trans (and thus can cleave other RNA molecules) under physiological conditions. Table I summarizes some of the characteristics of these ribozymes. In general, enzymatic nucleic acids act by first binding to a target RNA. Such binding occurs through the target binding portion of enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over other technologies, such as antisense technology (where a nucleic acid molecule generally simply binds to a nucleic acid target to block its translation) since the concentration of ribozyme necessary to affect a therapeutic treatment is lower than that of an antisense oligonucleotide. This advantage reflects the ability to the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf et al., 1992 *Proc. Natl. Acad. Sci. USA*, 89, 7305–7309). Thus, the specificity of action of a ribozyme is greater than that of an antisense oligonucleotide binding the same RNA site.

Van Tol et al., 1991 (*Virology* 180, 23) describe a hairpin ribozyme structure able to circularize. Hisamatsu et al., 1993 (*Nucleic Acids Symp. Ser.* 29, 173) describe hairpin ribozymes having a long substrate binding site in helix 1. Berzal-Herranz et al., 1993 (*EMBO J.* 12,2567) describe essential nucleotides in the hairpin ribozyme. Hampel and Tritz, 1989 (*Biochemistry* 28, 4929) describe a hairpin ribozyme derived from the minus strand of tobacco ringspot virus satellite [(−) sTRSV] RNA. Haseloff and Gerlach 1989 (*Gene* 82, 43) describe sequences required for self-cleavage reactions catalyzed by the (−) sTRSV RNA. Feldstein et al., 1989 (*Gene* 82, 53) tested various models oi trans-cleaving motifs derived from (−) sTRSV RNAs. The hairpin ribozyme can be assembled in various combinations to catalyze a unimolecular, bimolecular or a trimolecular cleavage/ligation reaction (Berzal-Herranz et al., 1992, *Genes & Develop.* 6, 129; Chowrira and Burke, 1992 *Nucleic Acids Res.* 20, 2835; Komatsu et al., 1993 *Nucleic Acids Res.* 21, 185; Komatsu et al., 1994 *J. Am. Chem. Soc*, 116, 3692). Increasing the length of helix 1 and helix 4 regions do not affect the catalytic activity of the hairpin ribozyme (Hisamatsu et al., 1993 supra; Chowrira and Burke, 1992 supra; Anderson et aL, 1994 *Nucleic Acids Res*, 22, 1096). For a review of various ribozyme motifs, and hairpin ribozyme in particular, see Ahsen and Schroeder, 1993 *Bioessays* 15, 299; Cech, 1992 *Curr. Opi. Struc. Bio.* 2, 605; and Hampel et aL, 1993 *Methods: A Companion to Methods in Enzymology* 5, 37.

This invention concerns an improved ribozyme based on the hairpin motif described by Hampel and Fritz 1989 supra; Feldstein et al., 1989 supra; Hampel et aL, 1990 *Nucleic Acid Rest* 18, 299; and Hampel et al., EP 0360257.

Hairpin ribozyme substrate complex comprises of two intermolecular helices formed between the ribozyme and the target RNA (helix 1 and helix 2). Length of helix 1 can be varied substantially without effecting the catalytic activity of the ribozyme (Hisamatsu et al., 1993 supra). However, the length of helix 2 is reported to be sensitive to variation. The length of helix 2 is normally between 3 and 5 base-pairs long (Hampel & Tritz, 1989 supra; Feldstein et al., 1989 supra; Haseloff and Gerlach, 1989 supra; Hampel et al., 1990 supra; Feldstein et al., 1990 *Proc. Natl. Acad. Sci. USA* 87, 2623). Several reports suggest that mutations within this helix significantly inhibit ribozyme activity (Hampel et al., 1990 supra; Feldstein et al., 1990 supra; Chowrira & Burke, 1991 *Biochemistry* 30, 8518; Joseph et al., 1993 *Genes & Develop.* 7, 130). It is also believed in the art that the length of helix 2 should be between 3 and 5 bp (Hampel et al., 1988 EPO 360 257; Hampel et al., 1993 supra, Cech, 1992 supra; von Ahsen and Schroeder, 1993 supra; Hisamatsu et al., 1993 supra, Anderson et al., 1994 supra).

SUMMARY OF THE INVENTION

This invention features an improved trans-cleaving hairpin ribozyme in which a new helix (i.e., a sequence able to form a double-stranded region with another single-stranded nucleic acid) is provided in the ribozyme to base-pair with a 5' region of a separate substrate nucleic acid. This helix is provided at the 3' end of the ribozyme after helix 3 as shown in FIG. 6. In addition, at least two extra bases may be provided in helix 2 and a portion of the substrate corresponding to helix 2 may be either directly linked to the 5' portion able to hydrogen bond to the 3' end of the hairpin or may have a linker of atleast one base. By trans-cleaving is meant that the ribozyme is able to act in trans to cleave another RNA molecule which is not covalently linked to the ribozyme itself. Thus, the ribozyme is not able to act on itself in an intramolecular cleavage reaction.

By "base-pair" is meant a nucleic acid that can form hydrogen bond(s) with other RNA sequence by either traditional Watson-Crick or other non-traditional types (for example Hoogsteen type) of interactions.

Referring to FIG. 6, there is shown in diagrammatic form the general structure of a ribozyme of this invention. Helix 2 (H2) is provided with a least 4 base pairs (i.e., n is 1, 2, 3 or 4) and a new helix 5 is provided of length 2 or more bases (preferably 3–20 bases, i.e., m is from 1–20 or more). Helix 2 and helix 5 may be covalently linked by one or more bases (i.e., r is≧1 base). Together, these modifications of the hairpin (HP) structure are advantageous in enhancing stability to the ribozyme-substrate complex. Helix 4 may also be extended by 2 or more base pairs (e.g., 4–10 base pairs) to stabilize the ribozyme structure. In each instances, each N and N' independently is any normal or modified base and each dash represents a potential base-pairing interaction. These nucleotides may be modified at the sugar, base or phosphate. Complete base-pairing is not required in the helixes, but is preferred. Helix 1 and 4 can be of any size (i.e., o and p is each independently from 0 to any number, e.g., 20) as long as some base-pairing is maintained. Essential bases are shown as specific bases in the structure, but those in the art will recognize that one or more may be modified chemically (abasic, base, sugar and/or phosphate modifications) or replaced with another base without significant effect. Helix 4 can be formed from two separate molecules, i.e., without a connecting loop. The connecting loop when present may be a ribonucleotide with or without modifications to its base, sugar or phosphate. "q" is $\geq 2$ bases. The connecting loop can also be replaced with a non-nucleotide linker molecule (see FIG. 17 for more details). H, refers to bases A, U or C. Y refers to pyrimidine bases. "———" refers to a chemical bond.

The increase in length of helix 2 of a hairpin ribozyme (with or without helix 5) has several advantages. These include improved stability of the ribozyme-target complex in vivo. In addition, an increase in the recognition sequence of the hairpin ribozyme improves the specificity of the ribozyme. This also makes possible the targeting of potential hairpin ribozyme sites that would otherwise be inaccessible due to neighboring secondary structure.

The increase in length of helix 2 of a hairpin ribozyme (with or without helix 5) enhances trans-ligation reaction catalyzed by the ribozyme. Transligation reactions catalyzed by the regular hairpin ribozyme (4 bp helix 2) is very inefficient (Komatsu et al., 1993 *Nucleic Acids Res.* 21, 185). This is attributed to weak base-pairing interactions between substrate RNAs and the ribozyme. By increasing the length of helix 2 (with or without helix 5) the rate of ligation (in vitro and in vivo) can be enhanced several fold.

Other features and advantages of the invention will be apparent from the following description of the preferred embodiments thereof, and from the claims.

DESCRIPTION OF PREFERRED EMBODIMENTS

The drawings will first briefly be described.
Drawings:

FIG. 2a is a diagrammatic representation of the hammerhead ribozyme domain known in the art;

FIG. 2b is a diagrammatic representation of the hammerhead ribozyme as divided by Uhlenbeck (1987, *Nature*, 327, 596–600) into a substrate and enzyme portion;

FIG. 2c is a similar diagram showing the hammerhead divided by Haseloff and Gerlach (1988, *Nature*, 334, 585–591) into two portions; and FIG. 2d is a similar diagram showing the hammerhead divided by Jeffries and Symons (1989, *Nucleic. Acids. Res.*, 17, 1371–1371) into two portions.

Figure 3:
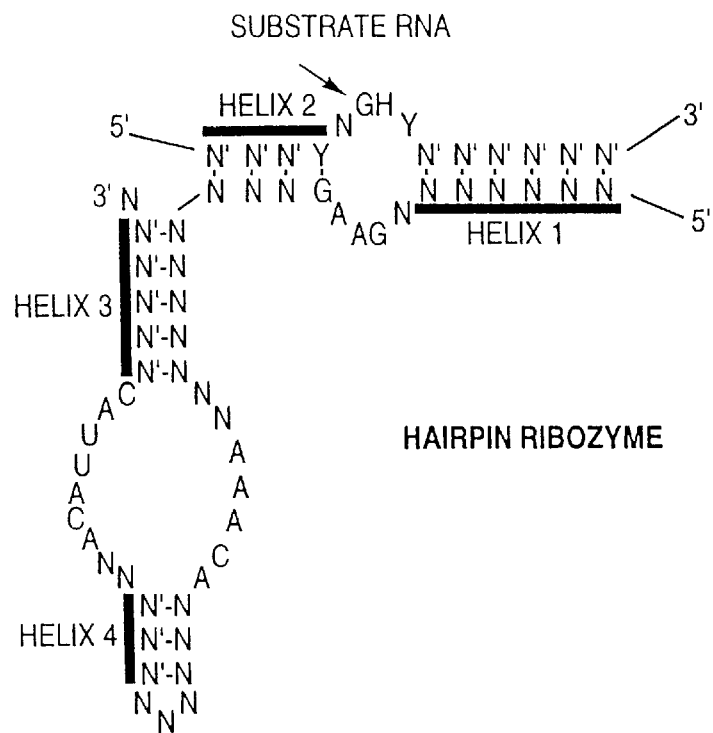

FIG. 3 is a representation of the general structure of the hairpin ribozyme domain known in the art. H, is A, U or C. Y is U or C. N is A, U, G, or C. N' is the complementary sequence of N. Helix 4 can be $\geq 2$ base-pair long.

Figure 4:
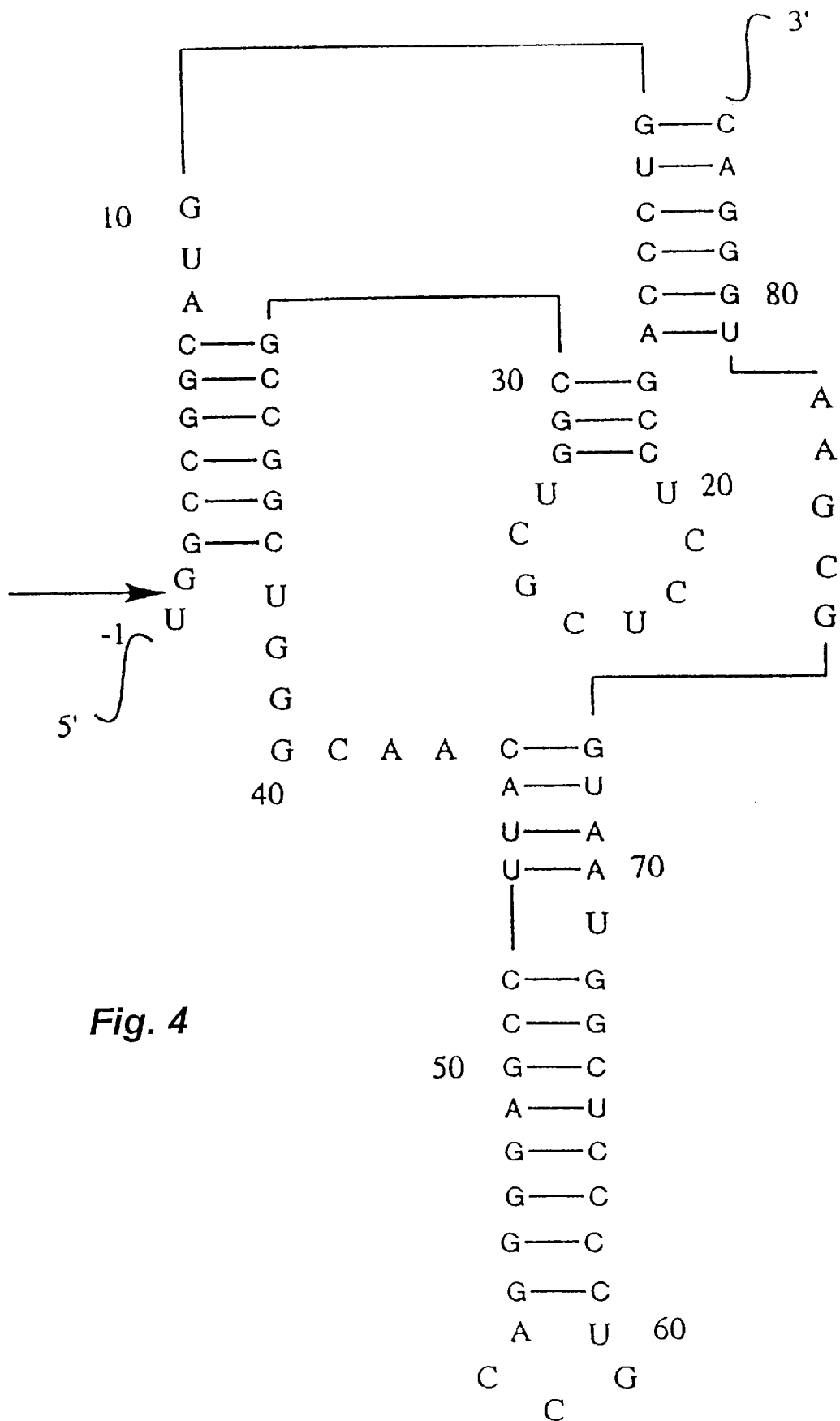

FIG. 4 is a representation of the general structure of the hepatitis delta virus ribozyme domain known in the art.

Figure 5:
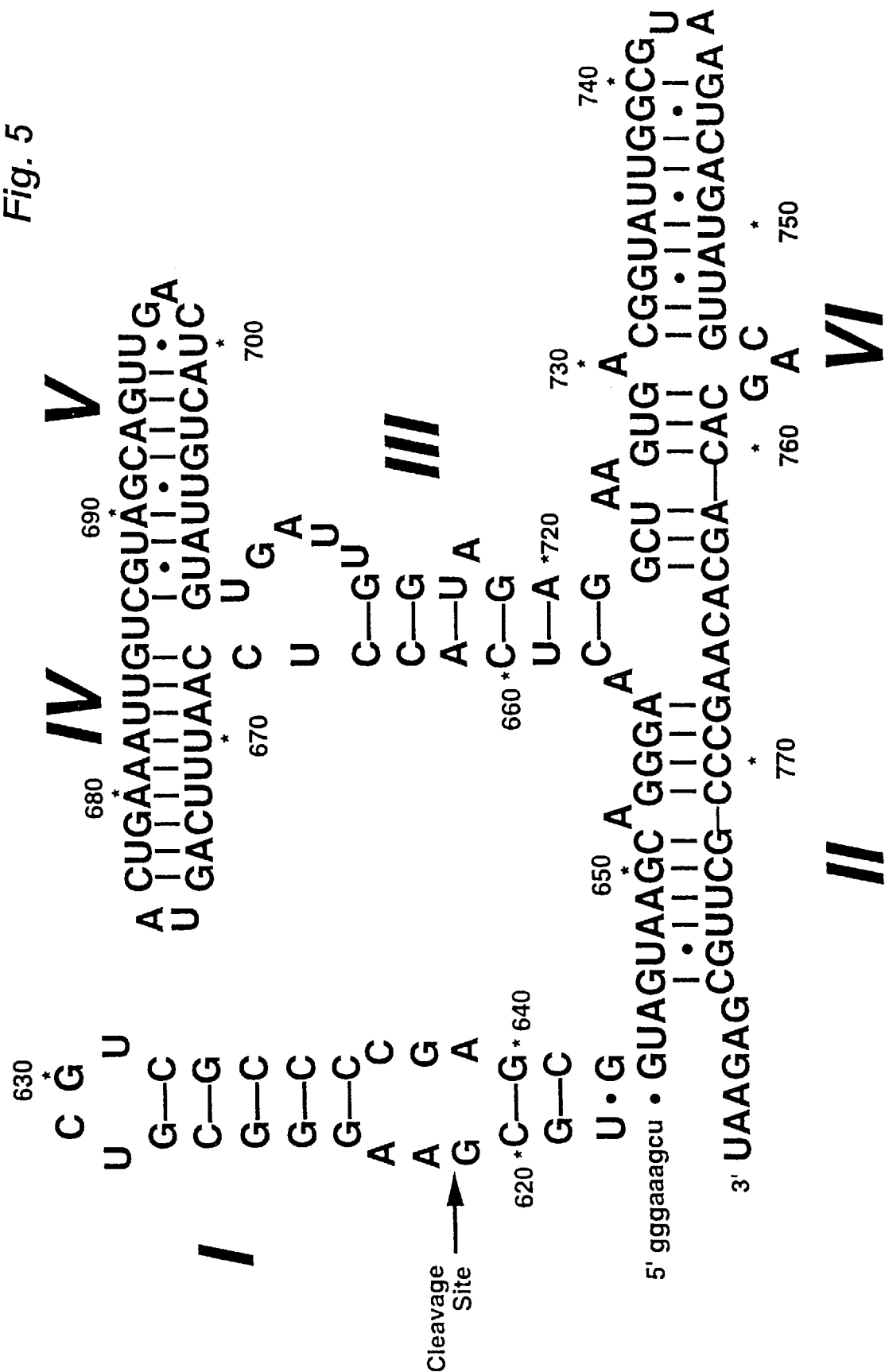

FIG. 5 is a representation of the general structure of the VS RNA ribozyme domain.

Figure 6:
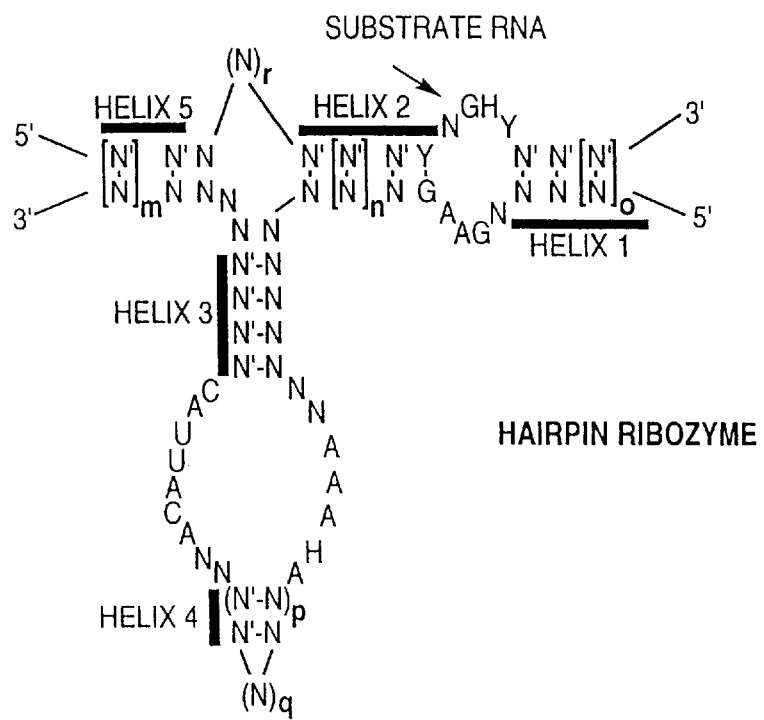

FIG. 6 is a diagrammatic representation of a ribozyme of this invention (see above for a complete description).

Figure 7A:
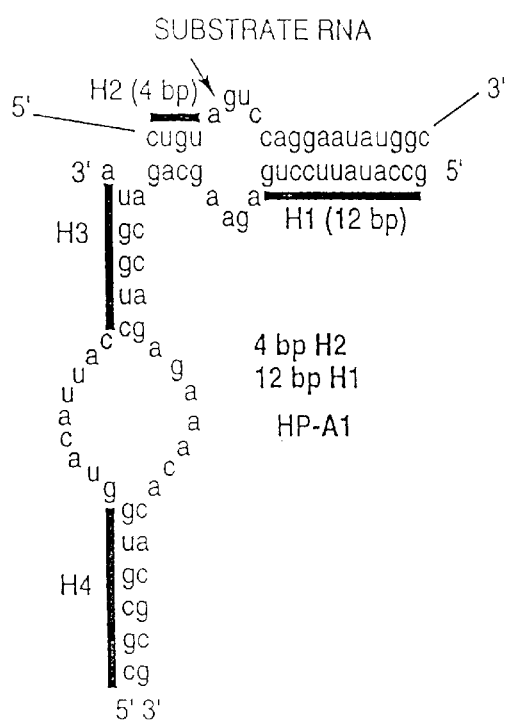
Figure 7B:
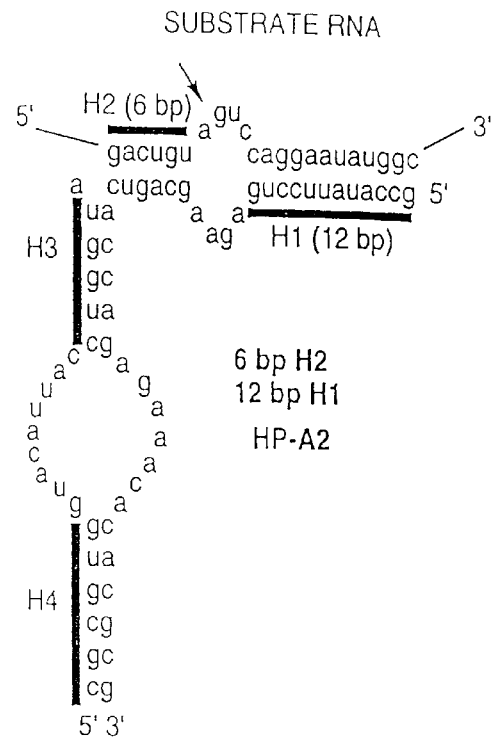

FIG. 7 is a diagrammatic representation of a Site A Hairpin Ribozyme (HP-A) showing the proposed secondary structure of the hairpin ribozyme substrate complex as described in the art (Berzal-Herranz et al., 1993 *EMBO. J.* 12, 2567). The ribozyme has been assembled from two fragments (bimolecular ribozyme; Chowrira and Burke, 1992 *Nucleic Acids Res.* 20, 2835); #H1 and H2 represent intermolecular helix formation between the ribozyme and the substrate. H3 and H4 represent intramolecular helix formation within the ribozyme (intermolecular helix in the case of bimolecular ribozyme). Left panel (HP-A1) indicates 4 base-paired helix 2 and the right panel (HP-A2) indicates 6 base-paired helix 2. Arrow indicates the site of RNA cleavage. All the ribozymes discussed herein were chemically synthesized by solid phase synthesis using RNA phosphoramadite chemistry, unless otherwise indicated. Those skilled in the art will recognize that these ribozymes could also be made transcriptionally in vitro and in vivo.

Figure 8:
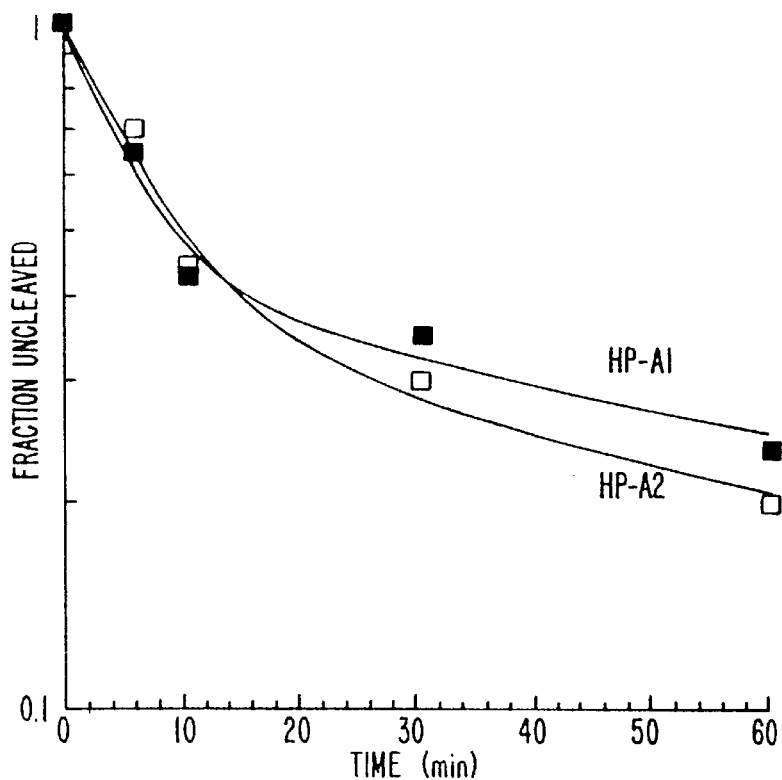

FIG. 8 of a graph showing RNA cleavage by hairpin ribozymes targeted to site A. A plot of fraction of the target RNA uncleaved (fraction uncleaved) as a function of time is shown. HP-A2 (6 bp helix 2) cleaves a 422 target RNA to a greater extent than the HP-A1 (4 bp helix 2).

To make internally-labeled substrate RNA for trans-ribozyme cleavage reactions, a 422 nt region (containing hairpin site A) was synthesized by PCR using primers that place the T7 RNA promoter upstream of the amplified sequence. Target RNA was transcribed in a standard transcription buffer in the presence of [$\alpha$-$^{32}$P]CTP (Chowrira & Burke, 1991 supra). The reaction mixture was treated with 15 units of ribonuclease-free DNaseI, extracted with phenol followed chloroform:isoamyl alcohol (25:1), precipitated with isopropanol and washed with 70% ethanol. The dried pellet was resuspended in 20 $\mu$l DEPC-treated water and stored at –20° C.

Unlabeled ribozyme (1 $\mu$M) and internally labeled 422 nt substrate RNA (<10 nM) were denatured and renatured separately in a standard cleavage buffer (containing 50 mM Tris.HCl pH 7.5 and 10 mM MgCl$_2$) by heating to 90° C. for 2 min. and slow cooling to 37° C. for 10 min. The reaction was initiated by mixing the ribozyme and substrate mixtures and incubating at 37° C. Aliquots of 5 $\mu$l were taken at regular time intervals, quenched by adding an equal volume of 2× formamide gel loading buffer and frozen on dry ice. The samples were resolved on 5% polyacrylamide sequencing gel and results were quantitatively analyzed by radio-analytic imaging of gels with a PhosphorImager (Molecular Dynamics, Sunnyvale, Calif.)

Figure 9A:
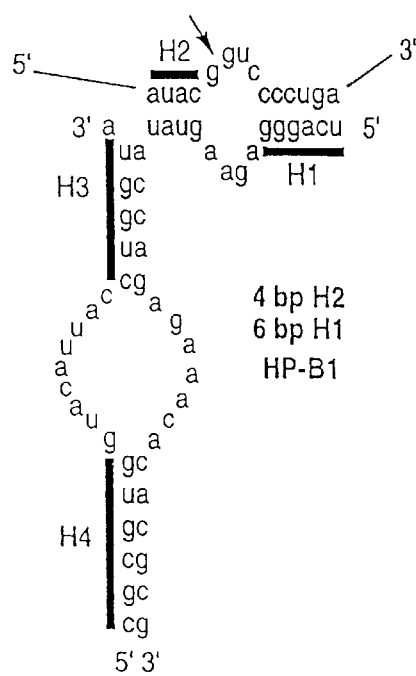
Figure 9B:
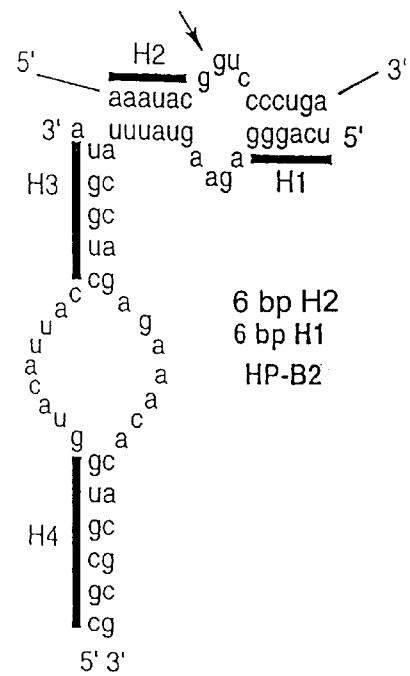

FIG. 9 is the Site B Hairpin Ribozyme (HP-B) showing proposed secondary structure of the hairpin ribozyme substrate complex. The ribozyme was assembled from two fragments as described above. The nomenclature is the same as above.

Figure 10:
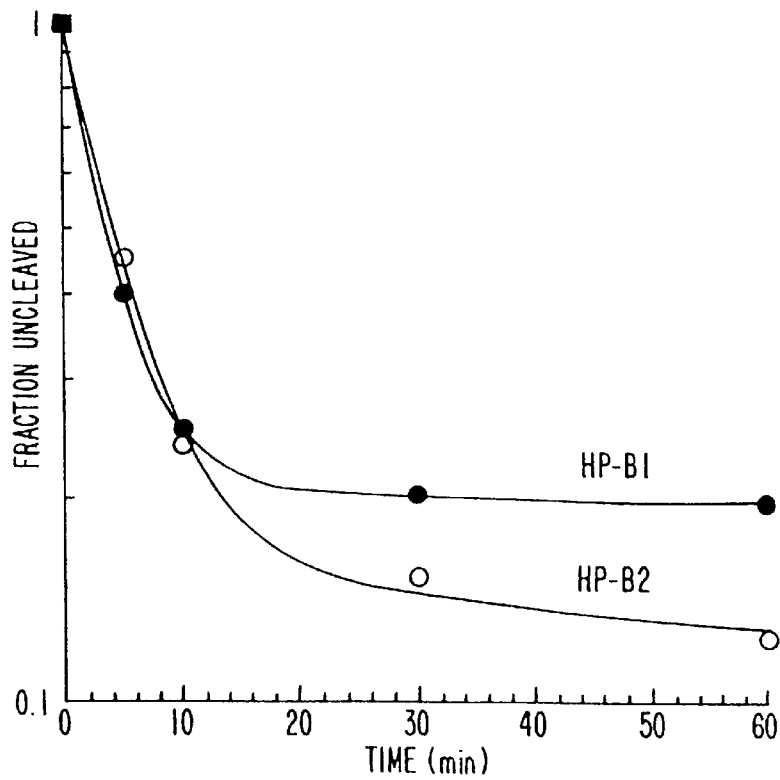

FIG. 10 a graph showing RNA cleavage by hairpin ribozymes targeted to site B. A. plot of fraction of the target RNA uncleaved (fraction uncleaved) as a function of time is shown. HP-B2 (6 bp helix 2) cleaves a 2 KB target RNA to a greater extent than the HP-B1 (4 bp helix 2). To make internally-labeled substrate RNA for trans-ribozyme cleavage reactions, a 2 kB region (containing hairpin site B) was synthesized by PCR using primers that place the T7 RNA promoter upstream of the amplified sequence. The cleavage reactions were carried out as described above.

Figure 11A:
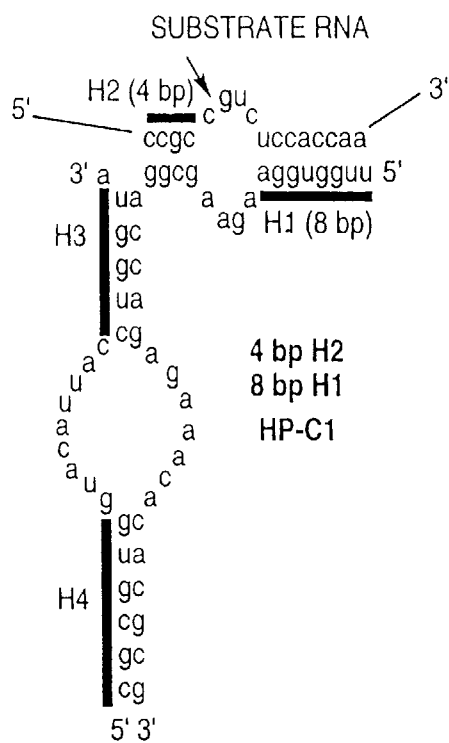
Figure 11B:
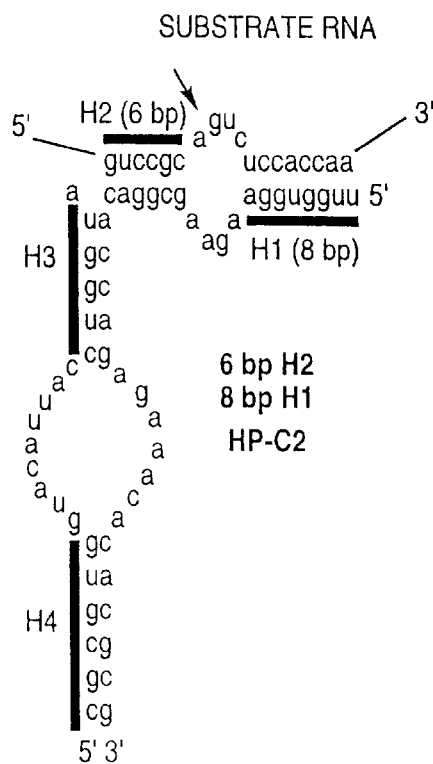

FIG. 11 shows a Site C Hairpin Ribozyme (HP-C) with the proposed secondary structure of the hairpin ribozyme substrate complex. The ribozyme was assembled from two fragments as described above.

Figure 12:
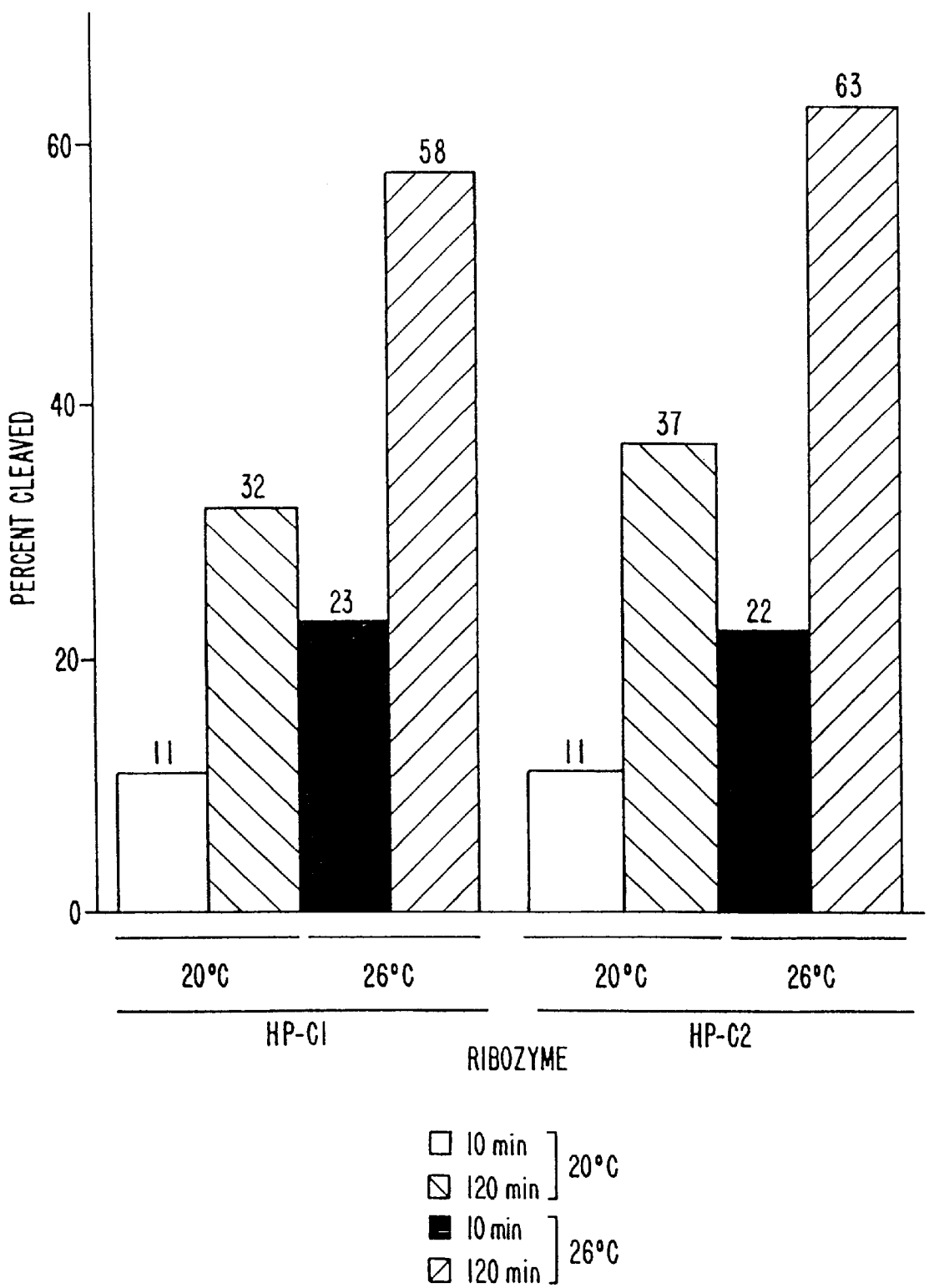

FIG. 12 is a graph showing RNA cleavage by hairpin ribozymes targeted to site C. The ribozymes were tested at both 20° C. and at 26° C. To make internally-labeled substrate RNA for trans-ribozyme cleavage reactions, a 1.9 KB region (containing hairpin site C) was synthesized by PCR using primers that place the T7 RNA promoter upstream of the amplified sequence. Cleavage reactions were carried out as described above except that 20° C. and at 26° C. temperatures were used.

Figure 13A:
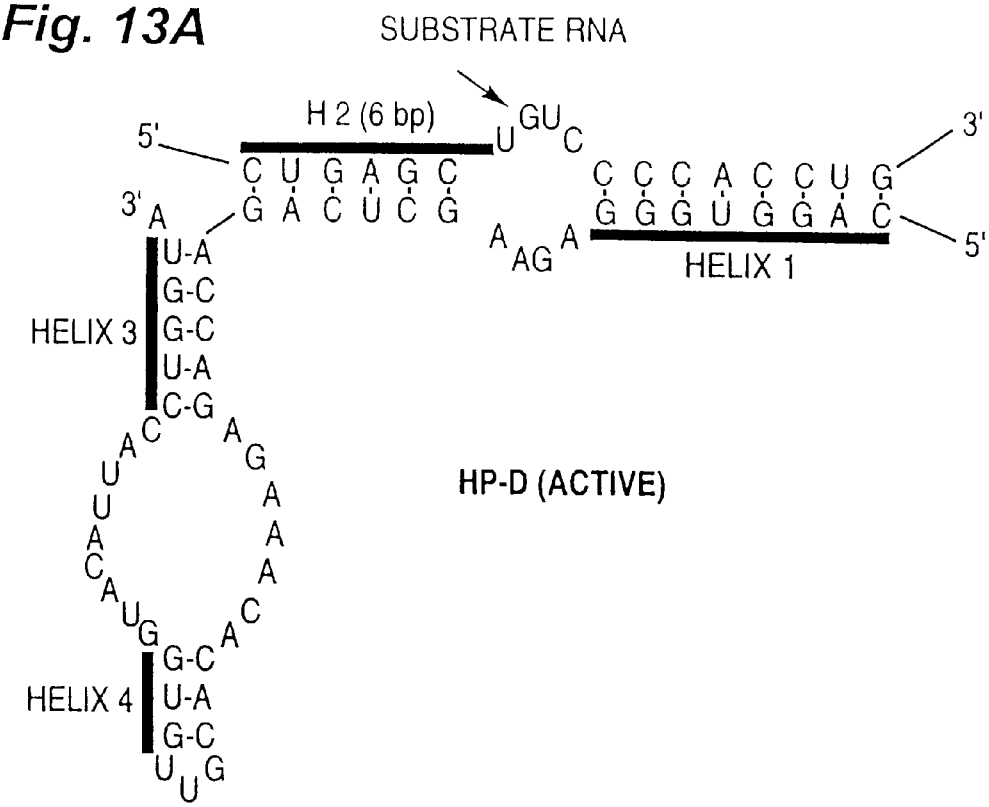
Figure 13B:
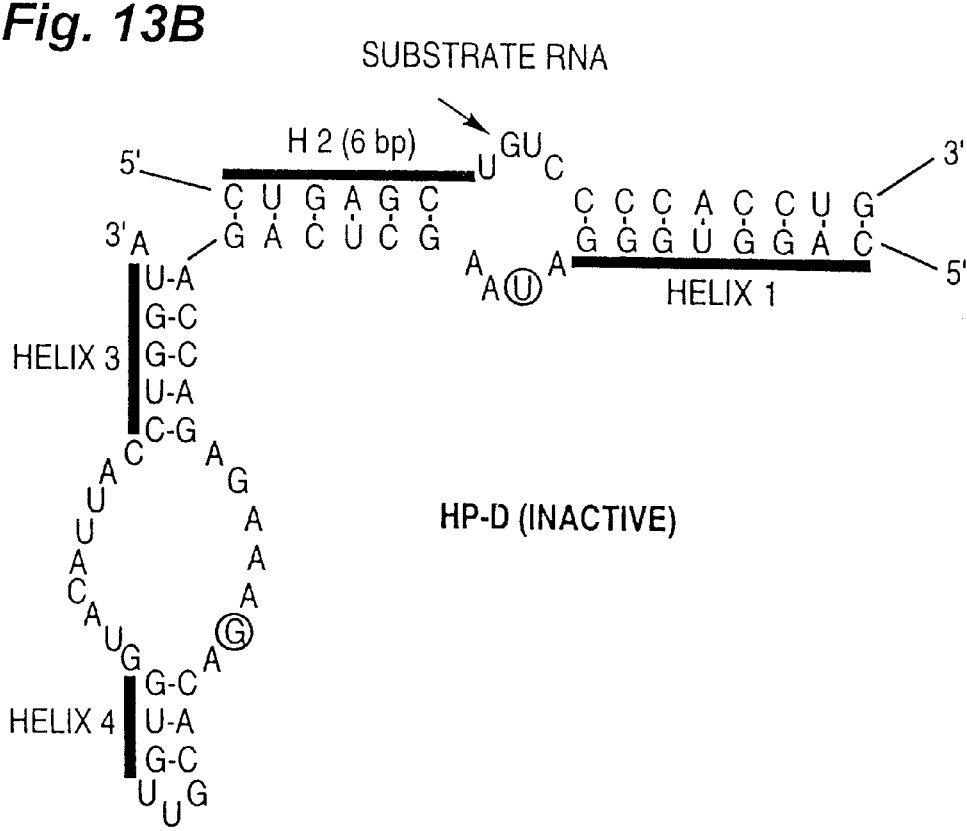
Figure 15A:
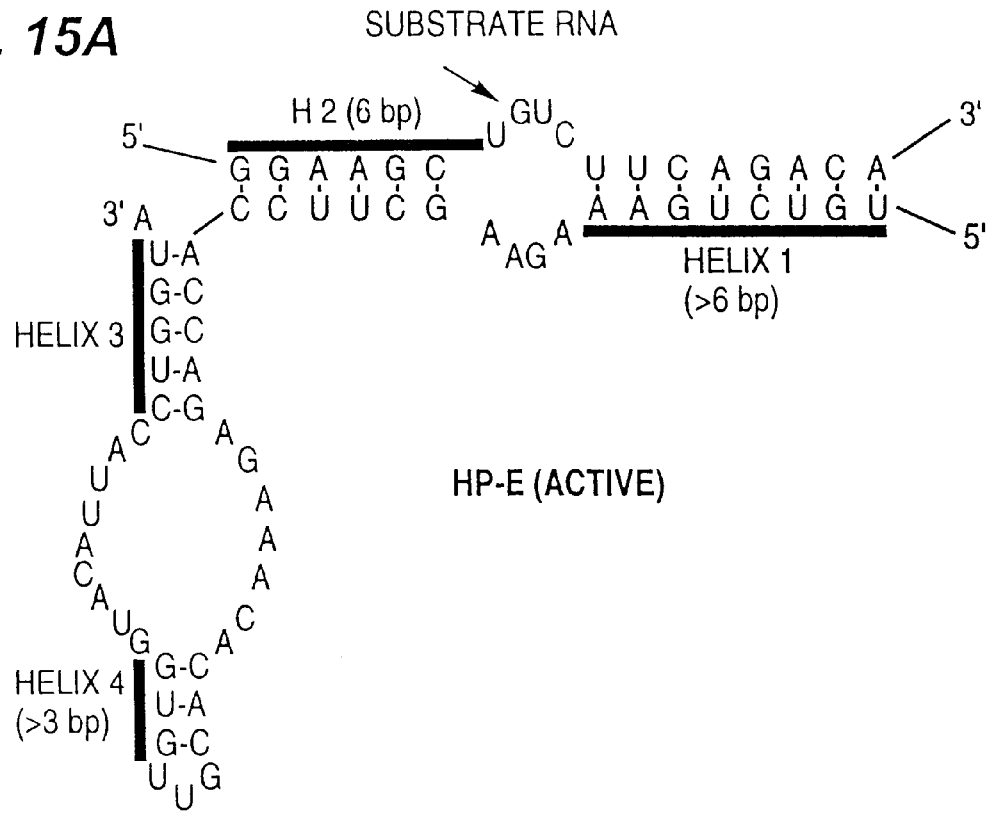
Figure 15B:
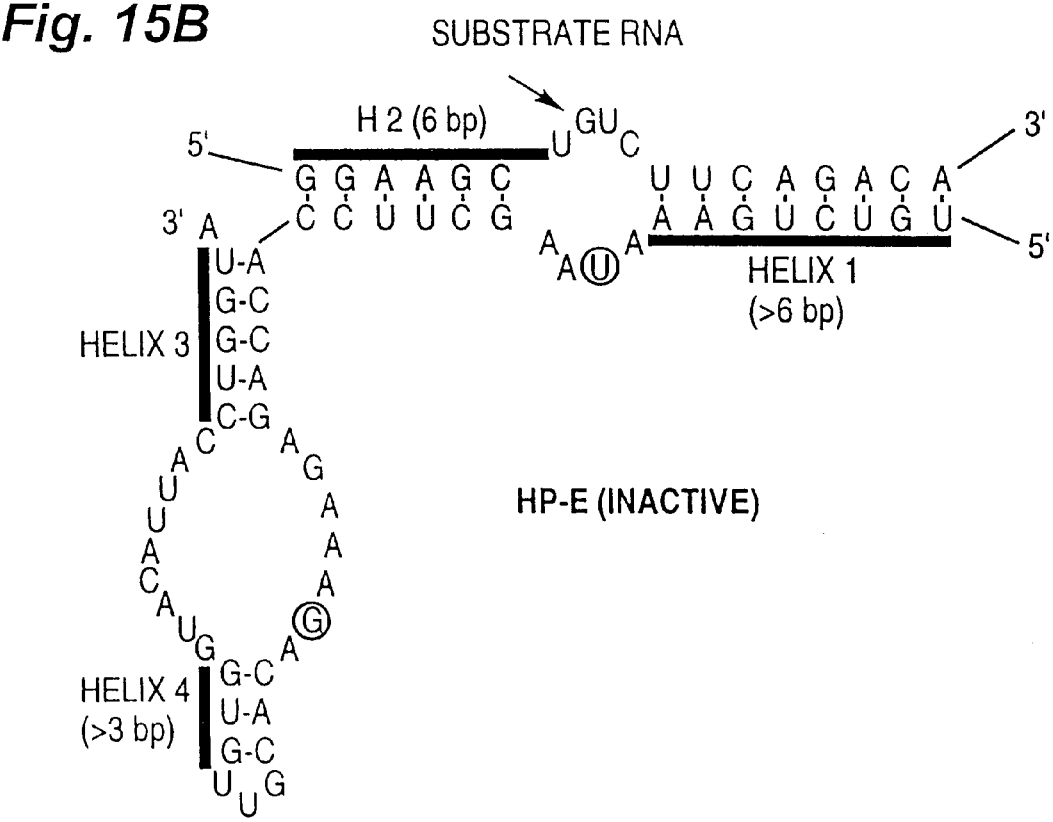
Figure 17A:
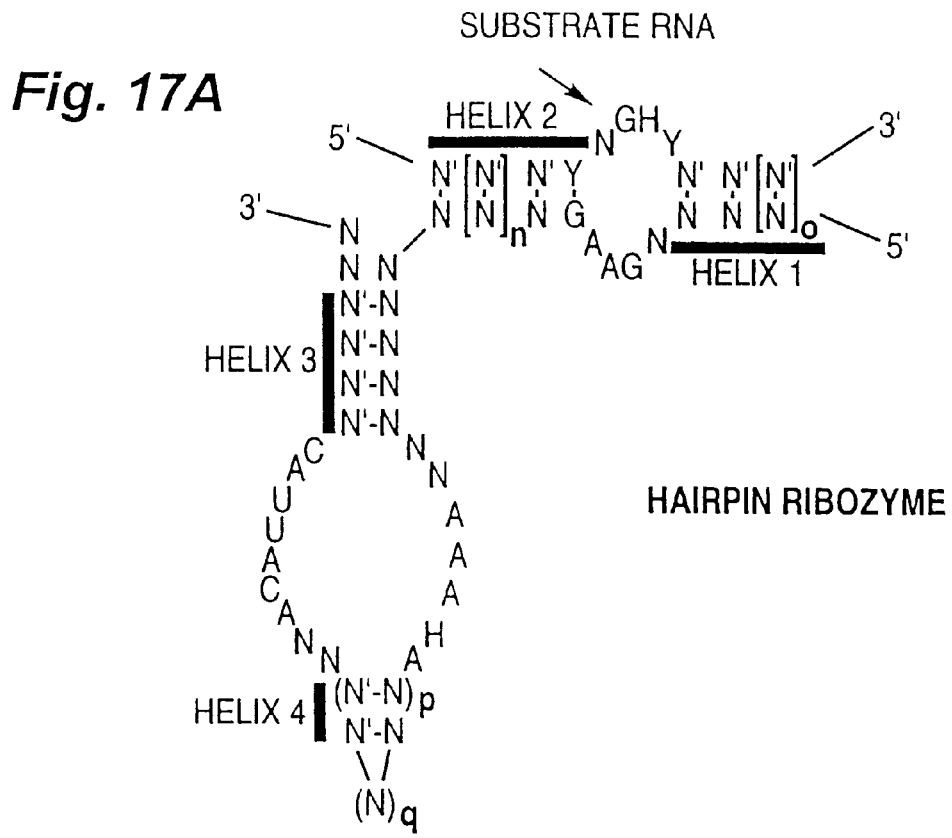
Figure 17B:
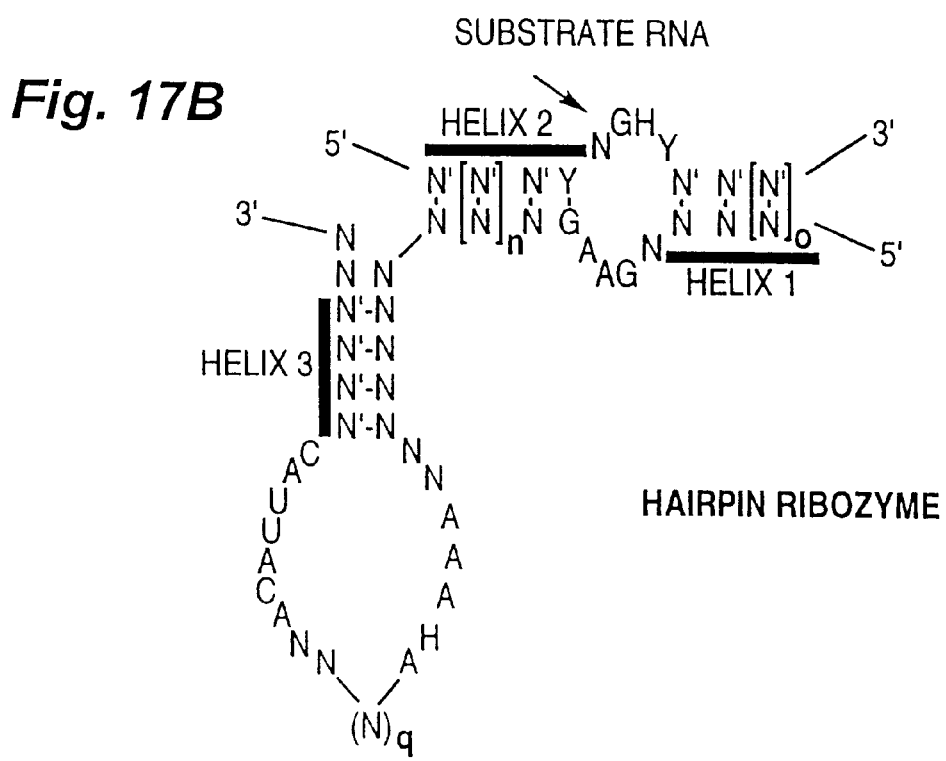
Figure 17C:
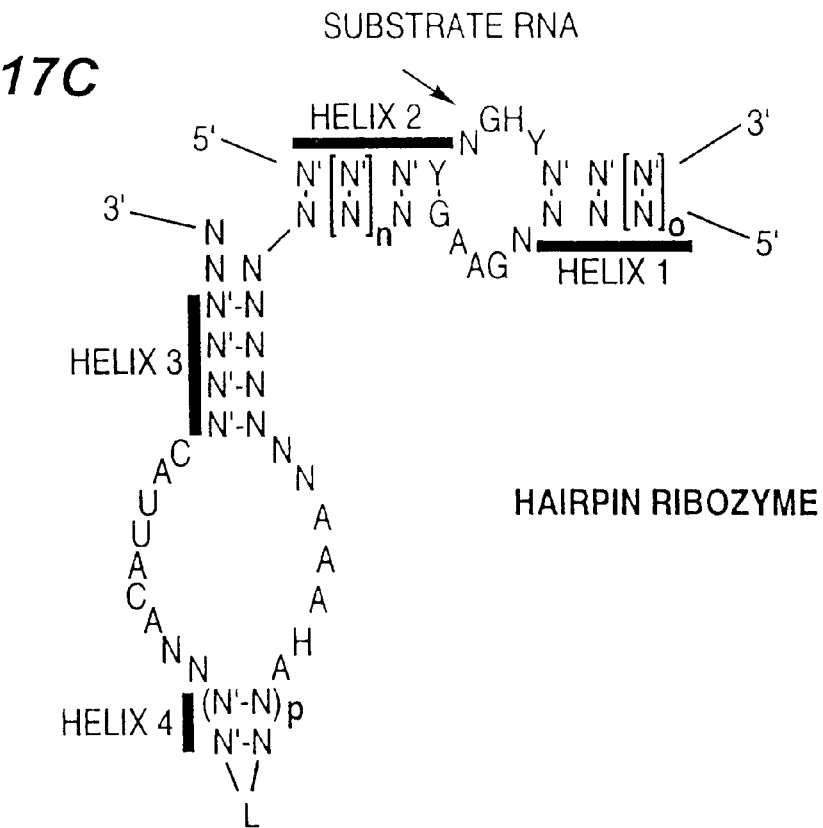
Figure 17D:
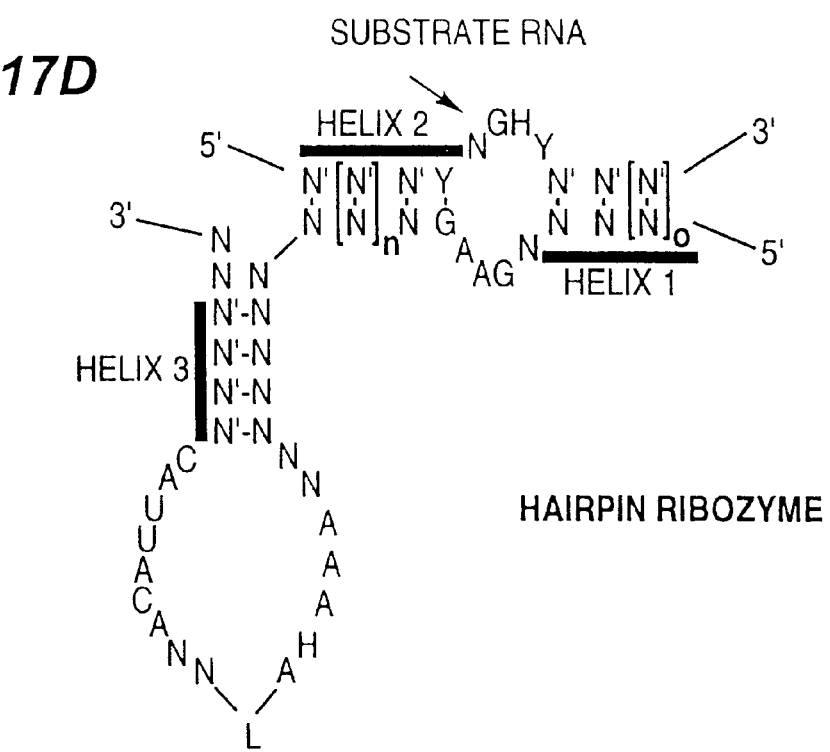

FIGS. 13 and 15 show Site D and E hairpin ribozymes (HP-D/E) within a proposed secondary structure of hairpin ribozyme substrate complex. Two hairpin ribozymes were designed to cleave two distinct sites (sites D and sites E) within the mouse TNF-α mRNA. Two more ribozymes were synthesized containing mutations in the catalytic core of the ribozyme which renders the ribozyme inactive (Berzal-Herranz et al., 1993 *EMBO J.* 12, 2567). To construct these ribozymes, partially overlapping top- and bottom-strand oligonucleotides (~50 nucleotides) were designed to include sequences for the T7 promoter and the hairpin ribozyme. The single-strand portions of annealed oligonucleotides were converted to double-strands using Sequenase® (U.S. Biochemicals). Transcription reactions containing linear double-stranded templates were carried out essentially as described (Milligan & Uhlenbeck, 1989 supra) using the T7 mega shortscript kit (Ambion, Austin, Tex.).

FIGS. 14 and 16 show RNA cleavage by HP-D and HP-E in mammalian cells with noted controls.

FIGS. 17A–17D shows various structural modifications of the present invention. A) Hairpin ribozyme lacking helix 5. Nomenclature is same as described under FIG. 6. B) Hairpin ribozyme lacking helix 4 and helix 5. Helix 4 is replaced by a nucleotide loop wherein q is ≧2 bases. Nomenclature is same as described under FIG. 6. C) Hairpin ribozyme lacking helix 5. Helix 4 loop is replaced by a linker "L", wherein L is a non-nucleotide linker molecule (Benseler et al., 1993 *J. Am. Chem. Soc.* 115, 8483; Jennings et al., WO 94/13688). Nomenclature is same as described under FIG. 6. D) Hairpin ribozyme lacking helix 4 and helix 5. Helix 4 is replaced by non-nucleotide linker molecule "L" (Benseler et al., 1993 supra; Jennings et al., supra). Nomenclature is same as described under FIG. 6.

Figure 18A:
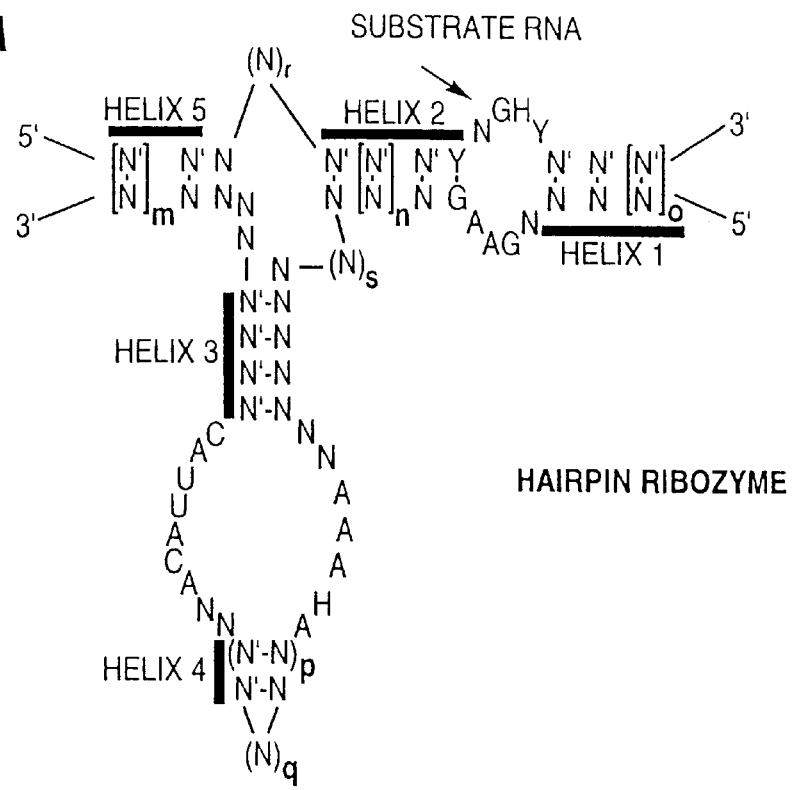
Figure 18B:
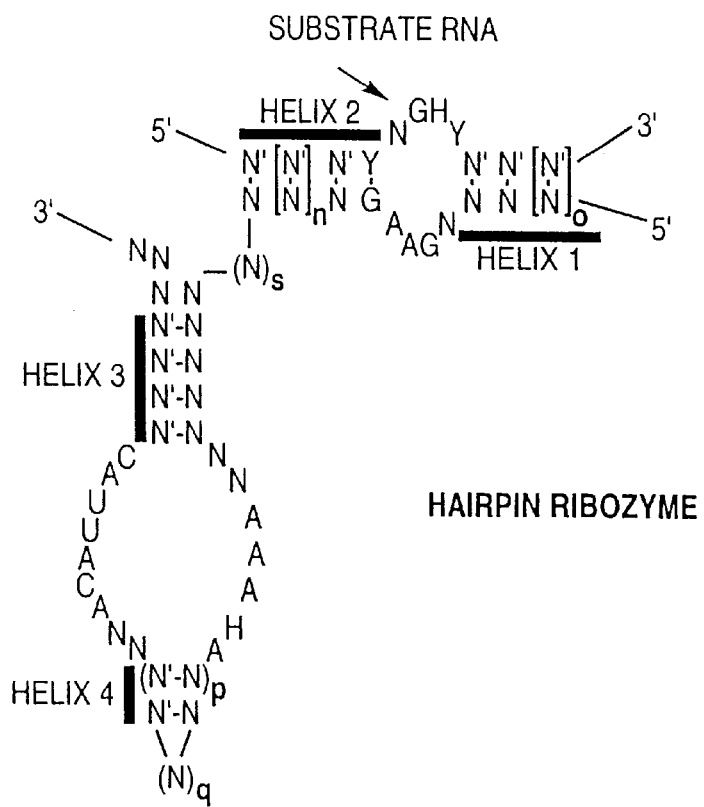

FIGS. 18A and B show Hairpin ribozymes containing nucleotide spacer region "s" at the indicated location, wherein s is ≧1 base. Hairpin ribozymes containing spacer region, can be synthesized as one fragment or can be assembled from multiple fragments. Nomenclature is same as described under FIG. 6.

TARGET SITES

Targets for useful ribozymes can be determined as disclosed in Draper et al. WO 93/23569, Sullivan et al., WO 94/02595 as well as by Draper et al., "Method and reagent for treatment of arthritic conditions U.S. Ser. No. 08/152,487, filed Nov. 12, 1993, abandoned, and hereby incorporated by reference herein in totality. Rather than repeat the guidance provided in those documents here, below are provided specific examples, not limiting to those in the art. Ribozymes to such targets are designed as described in those applications and synthesized to be tested in vitro and in vivo, as also described. Such ribozymes can also be optimized and delivered as described therein.

Ribozymes are designed to anneal to various sites in the target RNA. The binding arms are complementary to the target site sequences described above. The ribozymes are chemically synthesized. The method of synthesis used follows the procedure for normal RNA synthesis as described in Usman et al., 1987 *J. Am. Chem. Soc.*, 109, 7845–7854 and in Scaringe et al., 1990 *Nucleic Acids Res.*, 18, 5433–5441 and makes use of common nucleic acid protecting and coupling groups, such as dimethoxytrityl at the 5'-end, and phosphoramidites at the 3'-end. The average stepwise coupling yields were >98%. Hairpin ribozymes are synthesized in two parts and annealed to reconstruct the active ribozyme (Chowrira and Burke, 1992 *Nucleic Acids Res.*, 20, 2835–2840). All ribozymes are modified extensively to enhance stability by modification with nuclease resistant groups, for example, 2'-amino, 2'-C-allyl, 2'-flouro, 2'-o-methyl, 2'-H (for a review see Usman and Gedergren, 1992 TIBS 17, 34). Ribozymes are purified by gel electrophoresis using general methods or are purified by high pressure liquid chromatography (HPLC; See Usman et al., Synthesis, deprotection, analysis and purification of RNA and ribozymes, filed May, 18, 1994, U.S. Ser. No. 08/245,736, abandoned, the totality of which is hereby incorporated herein by reference) and are resuspended in water.

Ribozyme activity can be optimized by chemically synthesizing ribozymes with modifications that prevent their degradation by serum ribonucleases (see e.g., Eckstein et al., International Publication No. WO 92/07065; Perrault et al., *Nature* 1990, 344:565; Pieken et al., Science 1991, 253:314; Usman and Cedergren, *Trends in Biochem. Sci.* 1992, 17:334; Usman et al., International Publication No. WO 93/15187; and Rossi et al., International Publication No. WO 91/03162, as well as Usman, N. et al., U.S. patent application Ser. No. 07/829,729, U.S. Pat. No. 5,652,094, and Sproat, B. European Patent Application 92110298.4; Ortigao et al., 2 Antisense research and Development; Krist et al., Abstracts International conference on antisense nucleic acids, Garmisch-Partenkirchen, 1993; Chowrira and Burke, 1992 supra; Chowrira et al., 1993 *J. BioL Chem.* 268, 19458, which describe various chemical modifications that can be made to the sugar moieties of enzymatic RNA molecules. All these publications are hereby incorporated by reference herein.), modifications which enhance their efficacy in cells, and removal of helix-containing bases to shorten RNA synthesis times and reduce chemical requirements.

Ribozymes are added directly, or can be complexed with cationic lipids, packaged within liposomes, or otherwise delivered to target cells. The RNA or RNA complexes can be locally administered to relevant tissues ex viva, or in vivo through injection, aerosol inhalation, infusion pump or stent, with or without their incorporation in biopolymers.

Sullivan, et al., supra, describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination is locally delivered by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Sullivan, et al., supra and Draper, et al., supra which have been incorporated by reference herein.

Another means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein, O. and Moss, B., 1990, *Proc. Natl. Acad. Sci. U S A*, 87, 6743–7; Gao, X. and Huang; L., 1993, *Nucleic Acids Res.*, 21, 2867–72; Lieber, A., et al., 1993, *Methods Enzymol.*, 217, 47–66; Zhou, Y., et al., 1990, *Mol. Cell. Biol.*, 10, 4529–37). Several investigators have demonstrated that ribozymes expressed from such promoters can function in mammalian cells (e.g. (Kashani-Sabet, M., et al., 1992, *Antisense Res. Dev.*, 2, 3–15; Ojwang, J. O., et al., 1992, *Proc. Natl. Acad. Sci. U S A*, 89, 10802–6; Chen, C. J., et al., 1992, *Nucleic Acids Res.*, 20, 4581–9; Yu, M., et al., 1993, *Proc. Natl. Acad. Sci. U S A*, 90, 6340–4; L'Huillier, P. J., et al., 19921, *EMBO J.*, 11, 4411–8; Lisziewicz, J., et a., 1993, *Proc. Natl. Acad. Sci. U. S. A.*, 90, 8000–4)). The above ribozyme transcription units can be incorporated into a variety of vectors for introduction into mammalian cells, including but not restricted to, plasmid DNA vectors, viral DNA vectors (such as adenovirus or adeno-associated vectors), or viral RNA vectors (such as retroviral, Semliki forest virus, sindbis virus vectors).

In a preferred embodiment of the invention, a transcription unit expressing a hairpin ribozyme that cleaves target RNA (e.g., TNF-α mRNA) is inserted into a plasmid DNA vector or an adenovirus or adeno-associated DNA viral vector. Both viral vectors have been used to transfer genes to the lung and both vectors lead to transient gene expression (Zabner et al., 1993 *Cell* 75, 207; Carter, 1992 *Curr. Opi. Biotech.* 3, 533). The adenovirus vector is delivered as recombinant adenoviral particles. DNA may be delivered alone or complexed with vehicles (as described for RNA above). The DNA, DNA/vehicle complexes, or the recombinant adenovirus particles are locally administered to the site of treatment, e.g., through the use of an injection catheter, stent or infusion pump or are directly added to cells or tissues ex vivo.

In another aspect of the invention, ribozymes that cleave target molecules are expressed from transcription units inserted into DNA, RNA, or viral vectors. Preferably, the recombinant vectors capable of expressing the ribozymes are locally delivered as described above, and transiently persist in target cells. Once expressed, the ribozymes cleave the target mRNA. The recombinant vectors are preferably DNA plasmids, adenovirus, retroviral or adeno-associated virus vectors. However, other mammalian cell vectors that direct the expression of RNA may be used for this purpose.

Thus, ribozymes of the present invention that cleave target mRNA and thereby inhibit and/or reduce target activity have many potential therapeutic uses, and there are reasonable modes of delivering the ribozymes in a number of the possible indications. Development of an effective ribozyme that inhibits specific function are described in the art.

By "Inhibit" is meant that the activity or level of target RNA is reduced below that observed in the absence of the ribozyme, and preferably is below that level observed in the presence of an inactive RNA molecule able to bind to the same site on theRNA, but unable to cleave that RNA.

By "vectors" is meant any nucleic acid- and/or viral-based technique used to deliver a desired nucleic acid.

Diagnostic uses

Ribozymes of this invention may be used as diagnostic tools to examine genetic drift and mutations within diseased cells, or to detect specific RNA molecules, such as virus RNA. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These experiments will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes of this invention are well known in the art, and include detection of the presence of mRNA associated with a related condition. Such RNA is detected by determining the presence of a cleavage product after treatment with a ribozyme using standard methodology.

In a specific example, ribozymes which can cleave only wild-type or mutant forms of the target RNA are used for the assay. The first ribozyme is used to identify wild-type RNA present in the sample and the second ribozyme will be used to identify mutant RNA in the sample. As reaction controls, synthetic substrates of both wild-type and mutant RNA will be cleaved by both ribozymes to demonstrate the relative ribozyme efficiencies in the reactions and the absence of cleavage of the "non-targeted" RNA species. The cleavage products from the synthetic substrates will also serve to generate size markers for the analysis of wild-type and mutant RNAs in the sample population. Thus each analysis will require two ribozymes, two substrates and one unknown sample which will be combined into six reactions. The presence of cleavage products will be determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype is adequate to establish risk. If probes of comparable specific activity are used for both transcripts, then a qualitative comparison of RNA levels will be adequate and will decrease the cost of the initial diagnosis. Higher mutant form to wild-type ratios will be correlated with higher risk whether RNA levels are compared qualitatively or quantitatively.

EXAMPLES

Results of experiments suggest that the length of H2 can be 6 bp without significantly reducing the activity of the hairpin ribozyme. The H2 arm length variation does not appear to be sequence dependent. HP ribozymes with 6 bp H2 have been designed against five different target RNAs and all five ribozymes efficiently cleaved their cognate target RNA. Additionally, two of these ribozymes were able to successfully inhibit gene expression (e.g., TNF-α) in mammalian cells. Results of these experiments are shown below.

HP ribozymes with 7 and 8 bp H2 are also capable of cleaving target RNA in a sequence-specific manner, however, the rate of the cleavage reaction is lower than those catalyzed by HP ribozymes with 6 bp H2.

Example 1: 4 and 6 base pair H2

Referring to FIGS. 7–12, HP ribozymes were synthesized as described above and tested for activity. Surprisingly, those with 6 base pairs in H2 were still as active as those with 4 base pairs.

Example 2: TNF α ribozymes

Referring to FIGS. 13–16, hairpin ribozymes of this invention were synthesized as described, and tested in a mammalian cell system as described below.

Macrophage isolation. To produce responsive macrophages 1 ml of sterile fluid thioglycollate broth (Difco, Detroit, Mich.) was injected i.p. into 6 week old female C57bI/6NCRmice 3 days before peritoneal lavage. Mice were maintained as specific pathogen free in autoclaved cages in a laminar flow hood and given sterilized water to minimize "spontaneous" activation of macrophages. The resulting peritoneal exudate cells (PEC) were obtained by lavage using Hanks balanced salt solution (HBSS), plated at 2.5× $10^5$/well in 96 well plates (Costar, Cambridge, Mass.) with Eagles minimal essential medium (EMEM) with 10% heat inactivated fetal bovine serum. After adhering for 2 hours the wells were washed to remove non adherent cells. The resulting cultures were 97% macrophages as determined by morphology and staining for non-specific esterase.

Transfection of ribozymes into macrophages: The ribozymes were diluted to 2× final concentration, mixed with an equal volume of 11 nM lipofectamine (Life Technologies, Gaithersburg, Md.), and vortexed. 100 ml of lipid:ribozyme complex was then added directly to the cells, followed immediately by 10 ml fetal bovine serum. Three hours after ribozyme addition 100 ml of 1 mg/ml bacterial lipopolysaccharide (LPS) was added to each well to stimulate TNF production.

Quantitation of TNF-α in mouse macrophages: Supernatants were sampled at 0, 2, 4, 8, and 24 hours post LPS stimulation and stored at −70° C. until quantitation, which was done by a TNF-α specific ELISA. ELISA plates were coated with rabbit anti-mouse TNF-a serum at 1;1000 dilution (Genzyme) followed by blocking with blotto and incubation with TNF-α containing supernatants. TNF-α was then detected using a murine TNF-α specific hamster monoclonal antibody (Genzyme). The ELISA was developed with goat anti-hamster IgG coupled to alkaline phosphatase.

Assessment of reagent toxicity: Following ribozymellipid treatment of macrophages and harvesting of supernatants viability of the cells was assessed by incubation of the cells with 5 mg/ml of 3-(4,5-dimethylthiazol-2-yl)-2,5-diphenyl tetrazolium bromide (MTT). This compound is reduced by the mitochondrial dehydrogenases, the activity of which correlates well with cell viability. After 12 hours the absorbance of reduced MTT is measured at 585 nm.

Inhibition of TNF-α expression by hairpin ribozymes in mouse macrophages: As shown in FIGS. 14 and 16, expression of TNF-α is significantly inhibited by both active hairpin ribozymes HP-D and HP-E.

The inhibition of TNF-α expression appears to be dependent on the catalytic activity of the ribozyme, because, catalytically inactive hairpin ribozyme (HP-D dead) does not show appreciable inhibition. HP-E (inactive) ribozyme does show some inhibition of TNF-α expression at 162 nM ribozyme concentration. This inhibition may be attributed to some antisense effect.

Other embodiments are within the following claims.

TABLE I

Characteristics of Ribozymes

Group I Introns

Size: –200 to >1000 nucleotides.
Requires a U in the target sequence immediately 5' of the cleavage site.
Binds 4–6 nucleotides at 5' side of cleavage site.
Over 75 known members of this class. Found in Tetrahymena thermophila rRNA, fungal mitochondria, chloroplasts, phage T4, blue-green algae, and others.

RNAseP RNA (M1 RNA)

Size: –290 to 400 nucleotides.
RNA portion of a ribonucleoprotein enzyme. Cleaves tRNA precursors to form mature tRNA.
Roughly 10 known members of this group all are bacterial in origin.

Hammerhead Ribozyme

Figure 1:
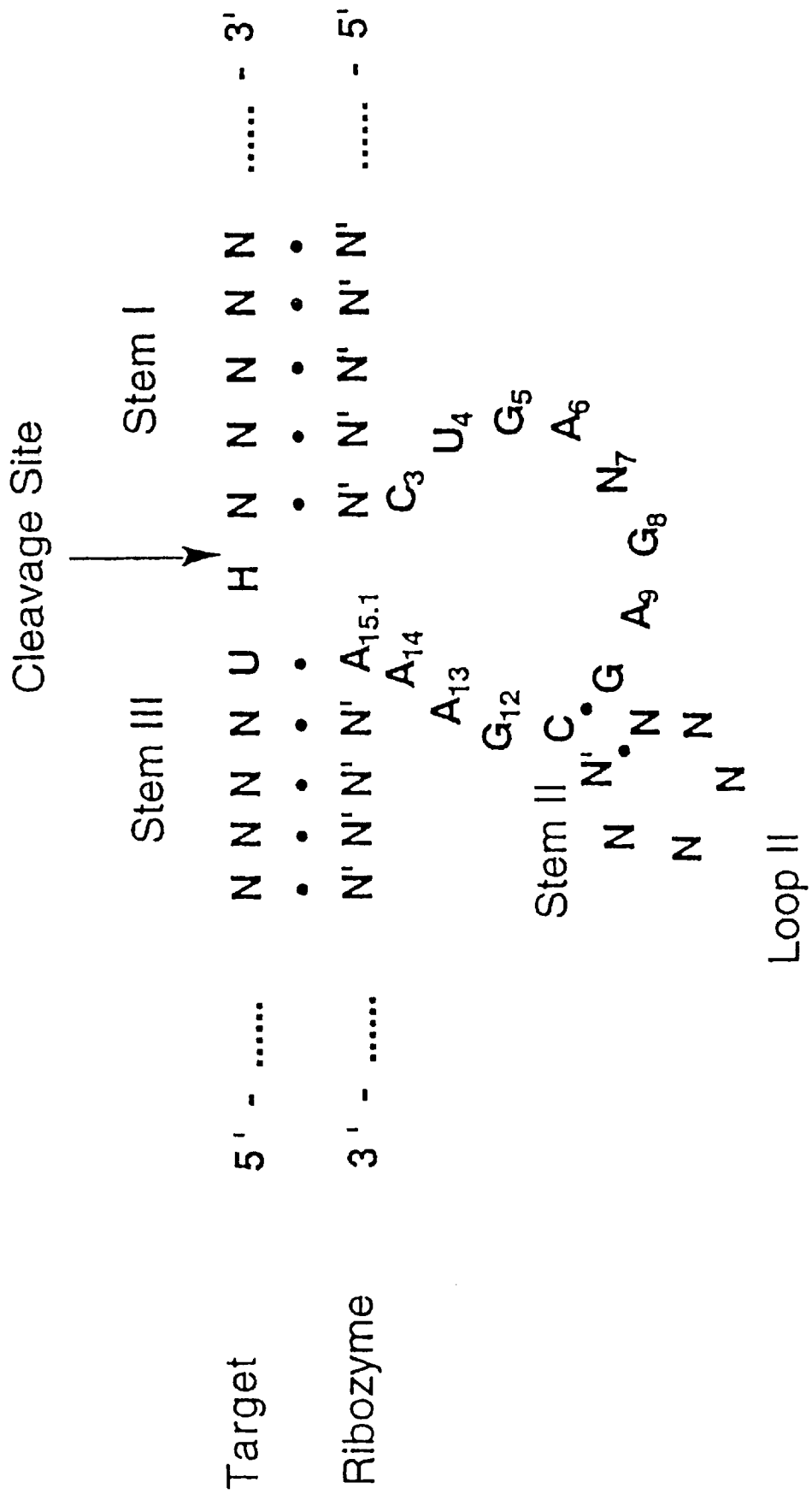
FIG. 1 is a diagrammatic representation of the hammerhead ribozyme domain known in the art. Stem II can be $\geq 2$ base-pair long, or can even lack base pairs and consist of a loop region.

Size: –13 to 40 nucleotides.
Requires the target sequence UH immediately 5' of the cleavage site.
Binds a variable number nucleotides on both sides of the cleavage site.
14 known members of this class. Found in a number of plant pathogens (virusoids) that use RNA as the infectious agent (FIG. 1)

Hairpin Ribozyme

Size: –50 nucleotides.
Requires the target sequence GUC immediately 3' of the cleavage site.
Binds 4–6 nucleotides at 5' side of the cleavage site and a variable number to the 3' side of the cleavage site.
Only 3 known member of this class. Found in three plant pathogen (satellite RNAs of the tobacco ringspot virus, arabis mosaic virus and chicory yellow mottle virus) which uses RNA as the infectious agent (FIG. 3).

Hepatitis Delta Virus (HDV) Ribozyme

Size: 50–60 nucleotides (at present).
Cleavage of target RNAs recently demonstrated.
Sequence requirements not fully determined.
Binding sites and structural requirements not fully determined, although no sequences 5' of cleavage site are required.
Only 1 known member of this class. Found in human HDV (FIG. 4).

Neuraspora VS RNA Ribozyme

Size: –144 nucleotides (at present)
Cleavage of target RNAs recently demonstrated.
Sequence requirements not fully determined.
Binding sites and structural requirements not fully determined. Only 1 known member of this class. Found in Neuraspara VS RNA (FIG. 5).

We claim:

1. A method of cleaving a separate RNA molecule comprising the step of contacting said separate RNA with a hairpin ribozyme comprising ribonucleotides, under conditions suitable for said cleaving, wherein said hairpin ribozyme comprises:
   (a) a helix 1 region comprising greater than or equal to three nucleotides inclusive, wherein said helix 1 region is complementary to a region of said separate RNA molecule;
   (b) a helix 2 region comprising between six and eight nucleotides inclusive, wherein said helix 2 region is complementary to a region of said separate RNA molecule;
   (c) a helix 3 region comprising nucleotides able to form at least four base-pairs; and
   (d) a helix 4 region comprising nucleotides able to form at least two base-pairs.

2. The method of claim 1, wherein said hairpin ribozyme comprises six nucleotides in the helix 2 region.

3. The method of claim 1, wherein said ribozyme has the following structure:

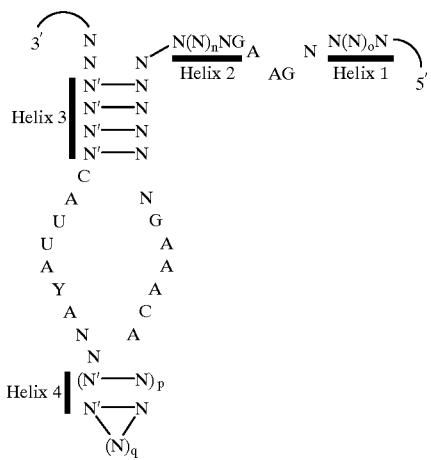

wherein each N and N' is independently any nucleotide;
   each A, U, G and C, is adenosine, uridine, guanosine and cytidine respectively and each Y is a pyrimidine nucleotide;
   each dash may represent a base-pair;
   p is 1–20, q is 2–20 when present, o is 1–20, n is 3–5; and the lines at the 3' and the 5'-ends of the ribozyme are meant to indicate additional nucleotides which may be present or absent.

4. The method of claim 1, wherein said hairpin ribozyme has the following structure:

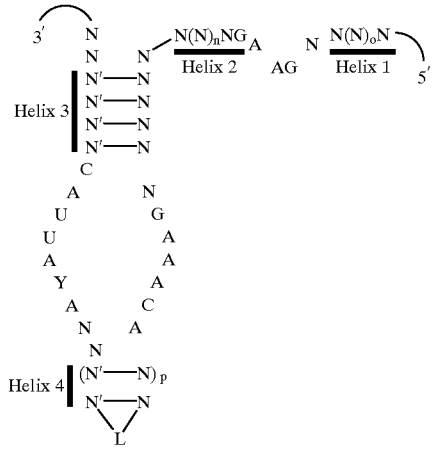

wherein each N and N' is independently any nucleotide;
   each A, U, G and C, is adenosine, uridine, guanosine and cytidine respectively and each Y is a pyrimidine nucleotide;
   each dash may represent a base-pair;
   p is 1–20, o is 1–20, n is 3–5;
   L is a non-nucleotide linker; and
   the lines at the 3' and the 5'-ends of the ribozyme are meant to indicate additional nucleotides which may be present or absent.

5. The method of claim 1, wherein said hairpin ribozyme comprises at least one sugar modification.

6. The method of claim 1, wherein said hairpin ribozyme comprises at least one nucleotide base modification.

7. The method of claim 1, wherein said hairpin ribozyme comprises at least one phosphate backbone modification.

8. The method of claim 1, wherein said hairpin ribozyme is chemically synthesized.

9. The method of claim 1, wherein said cleaving of said separate RNA molecule occurs in the presence of $Mg^{2+}$.

10. The method of claim 1, wherein said contacting of the separate RNA molecule with the hairpin ribozyme is in vitro.

11. The method of claim 1, wherein said contacting of the separate RNA molecule with the hairpin ribozyme is in a mammalian cell.

12. The method of claim 11, wherein said mammalian cell is a human cell.

* * * * *

SEQUENCE LISTING (1) GENERAL INFORMATION:

(iii) NUMBER OF SEQUENCES: 48

(2) INFORMATION FOR SEQ ID NO: 1:

(i) SEQUENCE CHARACTERISTICS:
      (A) LENGTH: 11 base pairs
      (B) TYPE: nucleic acid
      (C) STRANDEDNESS: single
      (D) TOPOLOGY: linear (ix) FEATURE:
      (D) OTHER INFORMATION: The letter "N" stands for any base.
          The letter "H" stands for C, A or U.

(xi) SEQUENCE DESCRIPTION: SEQ ID NO: 1:

NNNNUHNNNN N                                                        11

(2) INFORMATION FOR SEQ ID NO: 2:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (ix) FEATURE:
      (D) OTHER INFORMATION: The letter "N" stands for any base.

(xi) SEQUENCE DESCRIPTION: SEQ ID NO: 2:

NNNNNCUGAN GAGNNNNNNC GAAANNNN                         28

(2) INFORMATION FOR SEQ ID NO: 3:

(i) SEQUENCE CHARACTERISTICS:
      (A) LENGTH: 14 base pairs
      (B) TYPE: nucleic acid
      (C) STRANDEDNESS: single
      (D) TOPOLOGY: linear (ix) FEATURE:
      (D) OTHER INFORMATION: The letter "N" stands for any base.
          The letter "Y" is stands for U or C.
          The letter "H" stands for A, U or C.

(xi) SEQUENCE DESCRIPTION: SEQ ID NO: 3:

NNNYNGHYNN NNNN                                              14

(2) INFORMATION FOR SEQ ID NO: 4:

(i) SEQUENCE CHARACTERISTICS:
      (A) LENGTH: 50 base pairs
      (B) TYPE: nucleic acid
      (C) STRANDEDNESS: single
      (D) TOPOLOGY: linear (ix) FEATURE:
      (D) OTHER INFORMATION: The letter "N" stands for any base.

(xi) SEQUENCE DESCRIPTION: SEQ ID NO:4:

NNNNNNNGAA GNNNNNNNNN NAAACANNNN NNNNNNNACA UUACNNNNNN      50

(2) INFORMATION FOR SEQ ID NO: 5:

(i) SEQUENCE CHARACTERISTICS:
      (A) LENGTH: 85 base pairs

```
            (B) TYPE:              nucleic acid
            (C) STRANDEDNESS:      single
            (D) TOPOLOGY:          linear (xi) SEQUENCE DESCRIPTION: SEQ ID NO: 5:

UGGCCGGCAU GGUCCCAGCC UCCUCGCUGG CGCCGGCUGG GCAACAUUCC GAGGGGACCG      60

UCCCCUCGGU AAUGGCGAAU GGGAC                                           85

(2) INFORMATION FOR SEQ ID NO:   6:

(i) SEQUENCE CHARACTERISTICS:
            (A) LENGTH:            176 base pairs
            (B) TYPE:              nucleic acid
            (C) STRANDEDNESS:      single
            (D) TOPOLOGY:          linear (xi) SEQUENCE DESCRIPTION: SEQ ID NO: 6:

GGGAAAGCUU GCGAAGGGCG UCGUCGCCCC GAGCGGUAGU AAGCAGGGAA CUCACCUCCA      60

AUUUCAGUAC UGAAAUUGUC GUAGCAGUUG ACUACUGUUA UGUGAUUGGU AGAGGCUAAG     120

UGACGGUAUU GGCGUAAGUC AGUAUUGCAG CACAGCACAA GCCCGCUUGC GAGAAU        176

(2) INFORMATION FOR SEQ ID NO:   7:

(i) SEQUENCE CHARACTERISTICS:
            (A) LENGTH:            15 base pairs
            (B) TYPE:              nucleic acid
            (C) STRANDEDNESS:      single
            (D) TOPOLOGY:          linear (ix) FEATURE:
            (D) OTHER INFORMATION:  The letter "N" stands for any base.
                The letter "Y" is stands for U or C.
                The letter "H" stands for A, U or C.

(xi) SEQUENCE DESCRIPTION: SEQ ID NO: 7:

NNNNNNNYNG HYNNN                                                      15

(2) INFORMATION FOR SEQ ID NO:   8:

(i) SEQUENCE CHARACTERISTICS:
            (A) LENGTH:            47 base pairs
            (B) TYPE:              nucleic acid
            (C) STRANDEDNESS:      single
            (D) TOPOLOGY:          linear (ix) FEATURE:
            (D) OTHER INFORMATION:  The letter "N" stands for any base.
                The letter "H" stands for C, A or U.

(xi) SEQUENCE DESCRIPTION: SEQ ID NO: 8:

NNNNGAAGNN NNNNNNNNNA AAHANNNNNN NACAUUACNN NNNNNNN                   47

(2) INFORMATION FOR SEQ ID NO: 9:

(i) SEQUENCE CHARACTERISTICS:
            (A) LENGTH:            14 base pairs
            (B) TYPE:              nucleic acid
            (C) STRANDEDNESS:      single
            (D) TOPOLOGY:          linear (xi) SEQUENCE DESCRIPTION: SEQ ID NO: 9:

AUACGGUCCC CUGA                                                       14

(2) INFORMATION FOR SEQ ID NO: 10:

(i) SEQUENCE CHARACTERISTICS:
            (A) LENGTH:            32 base pairs
```

```
            (B) TYPE:              nucleic acid
            (C) STRANDEDNESS:      single
            (D) TOPOLOGY:          linear (xi) SEQUENCE DESCRIPTION: SEQ ID NO: 10:

UCAGGGAGAA GUAUACCAGA GAAACACACG CG                                   32

(2) INFORMATION FOR SEQ ID NO: 11:

(i) SEQUENCE CHARACTERISTICS:
            (A) LENGTH:            21 base pairs
            (B) TYPE:              nucleic acid
            (C) STRANDEDNESS:      single
            (D) TOPOLOGY:          linear (xi) SEQUENCE DESCRIPTION: SEQ ID NO: 11:

CGCGUGGUAC AUUACCUGGU A                                               21

(2) INFORMATION FOR SEQ ID NO: 12:

(i) SEQUENCE CHARACTERISTICS:
            (A) LENGTH:            16 base pairs
            (B) TYPE:              nucleic acid
            (C) STRANDEDNESS:      single
            (D) TOPOLOGY:          linear (xi) SEQUENCE DESCRIPTION: SEQ ID NO: 12:

AAAUACGGUC CCCUGA                                                     16

(2) INFORMATION FOR SEQ ID NO: 13:

(i) SEQUENCE CHARACTERISTICS:
            (A) LENGTH:            34 base pairs
            (B) TYPE:              nucleic acid
            (C) STRANDEDNESS:      single
            (D) TOPOLOGY:          linear (xi) SEQUENCE DESCRIPTION: SEQ ID NO: 13:

UCAGGGAGAA GUAUUUACCA GAGAAACACA CGCG                                 34

(2) INFORMATION FOR SEQ ID NO: 14:

(i) SEQUENCE CHARACTERISTICS:
            (A) LENGTH:            21 base pairs
            (B) TYPE:              nucleic acid
            (C) STRANDEDNESS:      single
            (D) TOPOLOGY:          linear (xi) SEQUENCE DESCRIPTION: SEQ ID NO: 14:

CGCGUGGUAC AUUACCUGGU A                                               21

(2) INFORMATION FOR SEQ ID NO: 15:

(i) SEQUENCE CHARACTERISTICS:
            (A) LENGTH:            16 base pairs
            (B) TYPE:              nucleic acid
            (C) STRANDEDNESS:      single
            (D) TOPOLOGY:          linear (xi) SEQUENCE DESCRIPTION: SEQ ID NO: 15:

CCGCCGUCUC CACCAA                                                     16

(2) INFORMATION FOR SEQ ID NO: 16:

(i) SEQUENCE CHARACTERISTICS:
            (A) LENGTH:            34 base pairs
            (B) TYPE:              nucleic acid
```

```
          (C) STRANDEDNESS:        single
          (D) TOPOLOGY:            linear (xi) SEQUENCE DESCRIPTION: SEQ ID NO: 16:

UUGGUGGAAG AAGCGGACCA GAGAAACACA CGCG                              34

(2) INFORMATION FOR SEQ ID NO: 17:

(i) SEQUENCE CHARACTERISTICS:
          (A) LENGTH:              21 base pairs
          (B) TYPE:                nucleic acid
          (C) STRANDEDNESS:        single
          (D) TOPOLOGY:            linear (xi) SEQUENCE DESCRIPTION: SEQ ID NO: 17:

CGCGUGGUAC AUUACCUGGU A                                            21

(2) INFORMATION FOR SEQ ID NO: 18:

(i) SEQUENCE CHARACTERISTICS:
          (A) LENGTH:              18 base pairs
          (B) TYPE:                nucleic acid
          (C) STRANDEDNESS:        single
          (D) TOPOLOGY:            linear (xi) SEQUENCE DESCRIPTION: SEQ ID NO: 18:

GUCCGCCGUC UCCACCAA                                                18

(2) INFORMATION FOR SEQ ID NO: 19:

(i) SEQUENCE CHARACTERISTICS:
          (A) LENGTH:              36 base pairs
          (B) TYPE:                nucleic acid
          (C) STRANDEDNESS:        single
          (D) TOPOLOGY:            linear (xi) SEQUENCE DESCRIPTION: SEQ ID NO: 19:

UUGGUGGAAG AAGCGGACAC CAGAGAAACA CACGCG                            36

(2) INFORMATION FOR SEQ ID NO: 20:

(i) SEQUENCE CHARACTERISTICS:
          (A) LENGTH:              22 base pairs
          (B) TYPE:                nucleic acid
          (C) STRANDEDNESS:        single
          (D) TOPOLOGY:            linear (xi) SEQUENCE DESCRIPTION: SEQ ID NO: 20:

CGCGTUGGUA CAUUACCUGG UA                                           22

(2) INFORMATION FOR SEQ ID NO: 21:

(i) SEQUENCE CHARACTERISTICS:
          (A) LENGTH:              18 base pairs
          (B) TYPE:                nucleic acid
          (C) STRANDEDNESS:        single
          (D) TOPOLOGY:            linear (xi) SEQUENCE DESCRIPTION: SEQ ID NO: 21:

CUGAGCUGUC CCCACCUG                                                18

(2) INFORMATION FOR SEQ ID NO: 22:

(i) SEQUENCE CHARACTERISTICS:
          (A) LENGTH:              54 base pairs
          (B) TYPE:                nucleic acid
          (C) STRANDEDNESS:        single
```

(D) TOPOLOGY:            linear (xi) SEQUENCE DESCRIPTION: SEQ ID NO: 22:

CAGGUGGGAG AAGCUCAGAC CAGAGAAACA CACGUUGUGG UACAUUACCU GGUA        54

(2) INFORMATION FOR SEQ ID NO: 23:

(i) SEQUENCE CHARACTERISTICS:
            (A) LENGTH:              18 base pairs
            (B) TYPE:                nucleic acid
            (C) STRANDEDNESS:        single
            (D) TOPOLOGY:            linear (xi) SEQUENCE DESCRIPTION: SEQ ID NO: 23:

CUGAGCUGUC CCCACCUG                                                18

(2) INFORMATION FOR SEQ ID NO: 24:

(i) SEQUENCE CHARACTERISTICS:
            (A) LENGTH:              54 base pairs
            (B) TYPE:                nucleic acid
            (C) STRANDEDNESS:        single
            (D) TOPOLOGY:            linear (xi) SEQUENCE DESCRIPTION: SEQ ID NO: 24:

CAGGUGGGAU AAGCUCAGAC CAGAGAAAGA CACGUUGUGG UACAUUACCU GGUA        54

(2) INFORMATION FOR SEQ ID NO: 25:

(i) SEQUENCE CHARACTERISTICS:
            (A) LENGTH:              18 base pairs
            (B) TYPE:                nucleic acid
            (C) STRANDEDNESS:        single
            (D) TOPOLOGY:            linear (xi) SEQUENCE DESCRIPTION: SEQ ID NO: 25:

GGAAGCUGUC UUCAGACA                                                18

(2) INFORMATION FOR SEQ ID NO: 26:

(i) SEQUENCE CHARACTERISTICS:
            (A) LENGTH:              54 base pairs
            (B) TYPE:                nucleic acid
            (C) STRANDEDNESS:        single
            (D) TOPOLOGY:            linear (xi) SEQUENCE DESCRIPTION: SEQ ID NO: 26:

UGUCUGAAAG AAGCUUCCAC CAGAGAAACA CACGUUGUGG UACAUUACCU GGUA        54

(2) INFORMATION FOR SEQ ID NO: 27:

(i) SEQUENCE CHARACTERISTICS:
            (A) LENGTH:              18 base pairs
            (B) TYPE:                nucleic acid
            (C) STRANDEDNESS:        single
            (D) TOPOLOGY:            linear (xi) SEQUENCE DESCRIPTION: SEQ ID NO: 27:

GGAAGCUGUC UUCAGACA                                                18

(2) INFORMATION FOR SEQ ID NO: 28:

(i) SEQUENCE CHARACTERISTICS:
            (A) LENGTH:              54 base pairs
            (B) TYPE:                nucleic acid
            (C) STRANDEDNESS:        single
            (D) TOPOLOGY:            linear (xi) SEQUENCE DESCRIPTION: SEQ ID NO: 28:

UGUCUGAAAU AAGCUUCCAC CAGAGAAAGA CACGUUGUGG UACAUUACCU GGUA                                54

(2) INFORMATION FOR SEQ ID NO: 29:

(i) SEQUENCE CHARACTERISTICS:
        (A) LENGTH:           11 base pairs
        (B) TYPE:             nucleic acid
        (C) STRANDEDNESS:     single
        (D) TOPOLOGY:         linear (xi) SEQUENCE DESCRIPTION: SEQ ID NO: 29:

NNNYNGHYNN N                                                                              11

(2) INFORMATION FOR SEQ ID NO: 30:

(i) SEQUENCE CHARACTERISTICS:
        (A) LENGTH:           43 base pairs
        (B) TYPE:             nucleic acid
        (C) STRANDEDNESS:     single
        (D) TOPOLOGY:         linear (ix) FEATURE:
        (D) OTHER INFORMATION:   The letter "N" stands for any base.
            The letter "H" stands for C, A or U.

(xi) SEQUENCE DESCRIPTION: SEQ ID NO: 30:

NNNNGAAGNN NNNNNNNNAA AHANNNNNNN ACAUUACNNN NNN                                            43

(2) INFORMATION FOR SEQ ID NO: 31:

(i) SEQUENCE CHARACTERISTICS:
        (A) LENGTH:           11 base pairs
        (B) TYPE:             nucleic acid
        (C) STRANDEDNESS:     single
        (D) TOPOLOGY:         linear (ix) FEATURE:
        (D) OTHER INFORMATION:   The letter "N" stands for any base.
            The letter "Y" is stands for U or C.
            The letter "H" stands for A, U or C.

(xi) SEQUENCE DESCRIPTION: SEQ ID NO: 31:

NNNYNGHYNN N                                                                              11

(2) INFORMATION FOR SEQ ID NO: 32:

(i) SEQUENCE CHARACTERISTICS:
        (A) LENGTH:           39 base pairs
        (B) TYPE:             nucleic acid
        (C) STRANDEDNESS:     single
        (D) TOPOLOGY:         linear (ix) FEATURE:
        (D) OTHER INFORMATION:   The letter "N" stands for any base.
            The letter "H" stands for C, A or U.

(xi) SEQUENCE DESCRIPTION: SEQ ID NO: 32:

NNNNGAAGNN NNNNNNNNAA AHANNNACAU UACNNNNNN                                                 39

(2) INFORMATION FOR SEQ ID NO: 33:

(i) SEQUENCE CHARACTERISTICS:
        (A) LENGTH:           11 base pairs
        (B) TYPE:             nucleic acid
        (C) STRANDEDNESS:     single
        (D) TOPOLOGY:         linear

```
    (ix) FEATURE:
          (D) OTHER INFORMATION:    The letter "N" stands for any base.
              The letter "Y" is stands for U or C.
              The letter "H" stands for A, U or C.

(xi) SEQUENCE DESCRIPTION: SEQ ID NO: 33:

NNNYNGHYNN N                                                                11

(2) INFORMATION FOR SEQ ID NO: 34:

(i) SEQUENCE CHARACTERISTICS:
          (A) LENGTH:             25 base pairs
          (B) TYPE:               nucleic acid
          (C) STRANDEDNESS:       single
          (D) TOPOLOGY:           linear (ix) FEATURE:
          (D) OTHER INFORMATION:    The letter "N" stands for any base.
              The letter "H" stands for C, A or U.

(xi) SEQUENCE DESCRIPTION: SEQ ID NO: 34:

NNNNGAAGNN NNNNNNNNAA AHANN                                                 25

(2) INFORMATION FOR SEQ ID NO: 35:

(i) SEQUENCE CHARACTERISTICS:
          (A) LENGTH:             17 base pairs
          (B) TYPE:               nucleic acid
          (C) STRANDEDNESS:       single
          (D) TOPOLOGY:           linear (ix) FEATURE:
          (D) OTHER INFORMATION:    The letter "N" stands for any base.

(xi) SEQUENCE DESCRIPTION: SEQ ID NO: 35:

NNNNACAUUA CNNNNNN                                                          17

(2) INFORMATION FOR SEQ ID NO: 36:

(i) SEQUENCE CHARACTERISTICS:
          (A) LENGTH:             11 base pairs
          (B) TYPE:               nucleic acid
          (C) STRANDEDNESS:       single
          (D) TOPOLOGY:           linear (ix) FEATURE:
          (D) OTHER INFORMATION:    The letter "N" stands for any base.
              The letter "Y" is stands for U or C.
              The letter "H" stands for A, U or C.

(xi) SEQUENCE DESCRIPTION: SEQ ID NO: 36:

NNNYNGHYNN N                                                                11

(2) INFORMATION FOR SEQ ID NO: 37:

(i) SEQUENCE CHARACTERISTICS:
          (A) LENGTH:             23 base pairs
          (B) TYPE:               nucleic acid
          (C) STRANDEDNESS:       single
          (D) TOPOLOGY:           linear (ix) FEATURE:
          (D) OTHER INFORMATION:    The letter "N" stands for any base.
              The letter "H" stands for C, A or U.

(xi) SEQUENCE DESCRIPTION: SEQ ID NO: 37:

NNNNGAAGNN NNNNNNNNAA AHA                                                   23

(2) INFORMATION FOR SEQ ID NO: 38:
```

```
    (i) SEQUENCE CHARACTERISTICS:
        (A) LENGTH:            15 base pairs
        (B) TYPE:              nucleic acid
        (C) STRANDEDNESS:      single
        (D) TOPOLOGY:          linear (ix) FEATURE:
        (D) OTHER INFORMATION:  The letter "N" stands for any base.

(xi) SEQUENCE DESCRIPTION: SEQ ID NO: 38:

NNACAUUACN NNNNN                                                        15

(2) INFORMATION FOR SEQ ID NO: 39:

(i) SEQUENCE CHARACTERISTICS:
        (A) LENGTH:            15 base pairs
        (B) TYPE:              nucleic acid
        (C) STRANDEDNESS:      single
        (D) TOPOLOGY:          linear (ix) FEATURE:
        (D) OTHER INFORMATION:  The letter "N" stands for any base.
            The letter "Y" is stands for U or C.
            The letter "H" stands for A, U or C.

(xi) SEQUENCE DESCRIPTION: SEQ ID NO: 39:

NNNNNNNYNG HYNNN                                                        15

(2) INFORMATION FOR SEQ ID NO: 40:

(i) SEQUENCE CHARACTERISTICS:
        (A) LENGTH:            47 base pairs
        (B) TYPE:              nucleic acid
        (C) STRANDEDNESS:      single
        (D) TOPOLOGY:          linear (ix) FEATURE:
        (D) OTHER INFORMATION:  The letter "N" stands for any base.
            The letter "H" stands for C, A or U.

(xi) SEQUENCE DESCRIPTION: SEQ ID NO: 40:

NNNNGAAGNN NNNNNNNNNA AAHANNNNNN NACAUUACNN NNNNNNN                     47

(2) INFORMATION FOR SEQ ID NO: 41:

(i) SEQUENCE CHARACTERISTICS:
        (A) LENGTH:            11 base pairs
        (B) TYPE:              nucleic acid
        (C) STRANDEDNESS:      single
        (D) TOPOLOGY:          linear (ix) FEATURE:
        (D) OTHER INFORMATION:  The letter "N" stands for any base.
            The letter "Y" is stands for U or C.
            The letter "H" stands for A, U or C.

(xi) SEQUENCE DESCRIPTION: SEQ ID NO: 41:

NNNYNGHYNN N                                                            11

(2) INFORMATION FOR SEQ ID NO: 42:

(i) SEQUENCE CHARACTERISTICS:
        (A) LENGTH:            45 base pairs
        (B) TYPE:              nucleic acid
        (C) STRANDEDNESS:      single
        (D) TOPOLOGY:          linear (ix) FEATURE:
        (D) OTHER INFORMATION:  The letter "N" stands for any base.
            The letter "H" stands for C, A or U.
```

(xi) SEQUENCE DESCRIPTION: SEQ ID NO: 42:

NNNNGAAGNN NNNNNNNNNA AAHANNNNNN NACAUUACNN NNNNN                          45

(2) INFORMATION FOR SEQ ID NO: 43:

(i) SEQUENCE CHARACTERISTICS:
            (A) LENGTH:            20 base pairs
            (B) TYPE:              nucleic acid
            (C) STRANDEDNESS:      single
            (D) TOPOLOGY:          linear (xi) SEQUENCE DESCRIPTION: SEQ ID NO: 43:

CUGUAGUCCA GGAAUAUGGC                                                      20

(2) INFORMATION FOR SEQ ID NO: 44:

(i) SEQUENCE CHARACTERISTICS:
            (A) LENGTH:            38 base pairs
            (B) TYPE:              nucleic acid
            (C) STRANDEDNESS:      single
            (D) TOPOLOGY:          linear (xi) SEQUENCE DESCRIPTION: SEQ ID NO: 44:

GCCAUAUUCC UGAGAAGCAG ACCAGAGAAA CACACGCG                                  38

(2) INFORMATION FOR SEQ ID NO: 45:

(i) SEQUENCE CHARACTERISTICS:
            (A) LENGTH:            21 base pairs
            (B) TYPE:              nucleic acid
            (C) STRANDEDNESS:      single
            (D) TOPOLOGY:          linear (xi) SEQUENCE DESCRIPTION: SEQ ID NO: 45:

CGCGUGGUAC AUUACCUGGU A                                                    21

(2) INFORMATION FOR SEQ ID NO: 46:

(i) SEQUENCE CHARACTERISTICS:
            (A) LENGTH:            22 base pairs
            (B) TYPE:              nucleic acid
            (C) STRANDEDNESS:      single
            (D) TOPOLOGY:          linear (xi) SEQUENCE DESCRIPTION: SEQ ID NO: 46:

GACUGUAGUC CAGGAAUAUG GC                                                   22

(2) INFORMATION FOR SEQ ID NO: 47:

(i) SEQUENCE CHARACTERISTICS:
            (A) LENGTH:            40 base pairs
            (B) TYPE:              nucleic acid
            (C) STRANDEDNESS:      single
            (D) TOPOLOGY:          linear (xi) SEQUENCE DESCRIPTION: SEQ ID NO: 47:

GCCAUAUUCC UGAGAAGCAG UCACCAGAGA AACACACGCG                                40

(2) INFORMATION FOR SEQ ID NO: 48:

(i) SEQUENCE CHARACTERISTICS:
            (A) LENGTH:            21 base pairs
            (B) TYPE:              nucleic acid
            (C) STRANDEDNESS:      single
            (D) TOPOLOGY:          linear (xi) SEQUENCE DESCRIPTION: SEQ ID NO: 48:

CGCGUGGUAC AUUACCUGGU A                                                         21